US010675382B2

(12) United States Patent
Sowa et al.

(10) Patent No.: US 10,675,382 B2
(45) Date of Patent: Jun. 9, 2020

(54) SCHWANN CELLS AND METHOD FOR PREPARING SAME

(71) Applicant: KYOTO PREFECTURAL PUBLIC UNIVERSITY CORPORATION, Kyoto (JP)

(72) Inventors: Yoshihiro Sowa, Kyoto (JP); Tsunao Kishida, Kyoto (JP); Osam Mazda, Kyoto (JP)

(73) Assignee: KYOTO PREFECTURAL PUBLIC UNIVERSITY CORPORATION, Kyoto (JP)

(*) Notice: Subject to any disclaimer, the term of this patent is extended or adjusted under 35 U.S.C. 154(b) by 0 days.

(21) Appl. No.: 15/509,912

(22) PCT Filed: Sep. 11, 2015

(86) PCT No.: PCT/JP2015/075921
§ 371 (c)(1),
(2) Date: Mar. 9, 2017

(87) PCT Pub. No.: WO2016/039462
PCT Pub. Date: Mar. 17, 2016

(65) Prior Publication Data
US 2017/0252484 A1 Sep. 7, 2017

(30) Foreign Application Priority Data

Sep. 12, 2014 (JP) .................. 2014-186210

(51) Int. Cl.
| | |
|---|---|
| *A61L 27/38* | (2006.01) |
| *C12N 5/079* | (2010.01) |
| *A61K 35/30* | (2015.01) |
| *A61L 27/00* | (2006.01) |
| *A61K 35/12* | (2015.01) |
| *C12N 15/09* | (2006.01) |
| *C12N 5/10* | (2006.01) |
| *A61P 25/00* | (2006.01) |
| *A61L 27/36* | (2006.01) |
| *A61L 27/54* | (2006.01) |

(52) U.S. Cl.
CPC .......... *A61L 27/383* (2013.01); *A61K 35/12* (2013.01); *A61K 35/30* (2013.01); *A61L 27/00* (2013.01); *A61L 27/3675* (2013.01); *A61L 27/3895* (2013.01); *A61L 27/54* (2013.01); *A61P 25/00* (2018.01); *C12N 5/0622* (2013.01); *C12N 5/10* (2013.01); *C12N 15/09* (2013.01); *A61L 2430/32* (2013.01); *C12N 2501/60* (2013.01); *C12N 2506/09* (2013.01); *C12N 2506/1384* (2013.01); *C12N 2506/28* (2013.01)

(58) Field of Classification Search
None
See application file for complete search history.

(56) References Cited

U.S. PATENT DOCUMENTS 6,989,271 B2 * 1/2006 Dezawa .............. A61L 27/383
424/93.7
2012/0100615 A1 * 4/2012 Tesar .................. C12N 5/0622
435/455

FOREIGN PATENT DOCUMENTS

CN 101318031 12/2008

OTHER PUBLICATIONS

Nawy, T. Transdifferentiation from the top. Nature Methods, vol. 12 No. 8, Aug. 2015, p. 701 (Year: 2015).*
Graf et al., Forcing cells to change lineages. Nature Reviews, vol. 462, Dec. 2009, pp. 587-594 (Year: 2009).*
Birchmeier et al., Neuregulin-1, a Key Axonal Signal that Drives Schwann Cell Growth and Differentiation. GLIA 56:1491-1497 (2008) (Year: 2008).*
Murphy et al., The regulation of Krox-20 expression reveals important steps in the control of peripheral glial cell development. Development 122, 2847-2857 (1996) (Year: 1996).*
Britsch et al., The transcription factor Sox10 is a key regulator of peripheral glial development. Genes & Development 15:66-78, 2001 (Year: 2001).*
Kim et al., Generation of Multipotent Induced Neural Crest by Direct Reprogramming of Human Postnatal Fibroblasts with a Single Transcription Factor. Cell Stem Cell, 15, 497-506, Oct. 2, 2014, published on-line Aug. 21, 2014 (Year: 2014).*
Thoma et al., Chemical Conversion of Human Fibroblasts into Functional Schwann Cells. Stem Cell Reports. 2014. vol. 3: 539-547 (Year: 2014).*
International Search Report dated Dec. 22, 2015 in corresponding International (PCT) Application No. PCT/JP2015/075921.
Yong Jun Kim et al., "Generation of Multipotent Induced Neural Crest by Direct Reprogramming of Human Postnatal Fibroblasts with a Single Transcription Factor", Cell Stem Cell, vol. 15, No. 4, 2014, pp. 497-506.
Reiprich et al., "Activation of Krox20 gene expression by Sox10 in myelinating Schwann cells", Journal of Neurochemistry, vol. 112, No. 3, 2010, pp. 744-754.
Yang et al., "Generation of oligodendroglial cells by direct lineage conversion", Nature Biotechnology, vol. 31, No. 5, 2013, pp. 434-439.
Najm et al., "Transcription factor-mediated reprogramming of fibroblasts to expandable, myelinogenic oligodendrocyte progenitor cells", Nature Biotechnology, vol. 31, No. 5, 2013, pp. 426-433.

(Continued)

*Primary Examiner* — Christopher M Babic
*Assistant Examiner* — Arthur S Leonard
(74) *Attorney, Agent, or Firm* — Wenderoth, Lind & Ponack, L.L.P.

(57) ABSTRACT

The present invention addresses the problem of providing a method for obtaining Schwann cells directly (by direct reprogramming) without passing through pluripotent stem cells, such as ES cells or iPS cells. As a means for solving this problem, the present invention provides a method for preparing Schwann cells that includes a step of introducing into somatic cells of a mammal at least one gene selected from the group consisting of SOX10 genes and KROX20 genes, or an expression product thereof.

2 Claims, 24 Drawing Sheets

(56) References Cited

OTHER PUBLICATIONS

Kingham et al., "Adipose-derived stem cells differentiate into a Schwann cell phenotype and promote neurite outgrowth in vitro", Experimental Neurology, vol. 207, No. 2, 2007, pp. 267-274.
Liu et al., "A new method for Schwann-like cell differentiation of adipose derived stem cells", Neuroscience Letters, vol. 551, 2013, pp. 79-83.
Hadlock et al., "A Polymer Foam Conduit Seeded with Schwann Cells Promotes Guided Peripheral Nerve Regeneration", Tissue Engineering, vol. 6, No. 2, 2000, pp. 119-127.
Jesuraj et al., "Schwann Cells Seeds in Acellular Nerve Grafts Improve Functional Recovery", Muscle Nerve, vol. 49, No. 2, 2014, pp. 267-276.
Tabesh et al., "The Role of biodegradable engineered scaffolds seeded with Schwann cells for spinal cord regeneration", Neurochemistry International, vol. 54, 2009, pp. 73-83.
Novikova et al., "Biodegradable poly-β-hydroxybutyrate scaffold seeded with Schwann cells to promote spinal cord repair", Biomaterials, vol. 29, No. 9, 2008, pp. 1198-1206.
Guest et al., "Clinical translation of autologous Schwann cell transplantation for the treatment of spinal cord injury", Current Opinion, vol. 18, No. 6, 2013, pp. 682-689.
Brook et al., "Extrusion Transplantation of Schwann Cells into the Adult Rat Thalamus Induces Directional Host Axon Growth", Experimental Neurology, vol. 126, No. 1, 1994, pp. 31-43.
Vaudano et al., "Change in the Molecular Phenotype of Schwann Cells Upon Transplantation into the Central Nervous System: Down-Regulation of C-Jun", Neuroscience, vol. 74, No. 2, 1996, pp. 553-565.
Keirstead et al., "Polysialylated Neural Cell Adhesion Molecule-Positive CNS Precursors Generate Both Oligodendrocytes and Schwann Cells to Remyelinate the CNS after Transplantation", The Journal of Neuroscience, vol. 19, No. 17, 1999, pp. 7529-7536.
Wan et al., "Schwann Cells Transplantation Promoted and the Repair of Brain Stem Injury in Rats", Biomedical and Environmental Sciences, vol. 16, No. 2, 2003, pp. 212-218.
Chen et al., "Treatment of Rat with Traumatic Brain Injury and MR Tracing In Vivo via Combined Transplantation of Bone Marrow Stromal Cells Labeled with Superparamagnetic Iron Oxide and Schwann Cells", Journal of Biomedical Nanotechnology, vol. 10, No. 2, 2014, pp. 205-215.
Shields et al., "Schwann Cell Remyelination is Restricted to Astrocyte-Deficient Areas After Transplantation Into Demyelinated Adult Rat Brain", Journal of Neuroscience Research, vol. 60, No. 5, 2000, pp. 571-578.
Masaki Ieda, "Heart regeneration using reprogramming technology", Proceedings of the Japan Academy, Ser. B, Physical and Biological Sciences, vol. 89, No. 3, 2013, pp. 118-128.
Ieda et al., "Direct Reprogramming of Fibroblasts into Functional Cardiomyocytes by Defined Factors", Cell, vol. 142, No. 3, 2010, pp. 375-386.
Qian et al., "In vivo reprogramming of murine cardiac fibroblasts into induced cardiomyocytes", Nature, vol. 485, 2012, pp. 593-598.
International Preliminary Report on Patentability dated Mar. 14, 2017 in corresponding International (PCT) Application No. PCT/JP2015/075921.
Extended European Search Report dated Mar. 23, 2018 in European Application No. 15839728.1.
Matsuse et al., "Human Umbilical Cord-Derived Mesenchymal Stromal Cells Differentiate Into Functional Schwann Cells That Sustain Peripheral Nerve Regeneration", J Neuropathol Exp Neurol, 69(9):973-985 (2010).
Keilhoff et al., "Transdifferentiation of mesenchymal stem cells into Schwann cell-like myelinating cells", European Journal of Cell Biology, 85(1):11-24 (2006).
Communication pursuant to Article 94(3) EPC dated Jul. 8, 2019 in corresponding European Patent Application No. 15839728.1.
Ghislain et al., "Neural crest patterning: autoregulatory and crest-specific elements co-operate for Krox20 transcriptional control", Development, 2003, vol. 130, No. 5, pp. 941-953.
Office Action dated Jan. 10, 2020 in corresponding Chinese Application No. 201580049009.4, 7 pages.

\* cited by examiner

%neuron bearing neurite

Longest neurite length (μm)

Number of neurites per neuron

Does dSC change to myelinated Schwann cells?

B. Macroscopic images of bridged nerves

Sham    Cont    cSC    dSC

C. Myelin stain images of the transverse section of regenerating nerve tissue

Sham    cSC    dSC

D. SFI (sciatic functional index)

E. Atrophy and fibrosis of innervated muscle

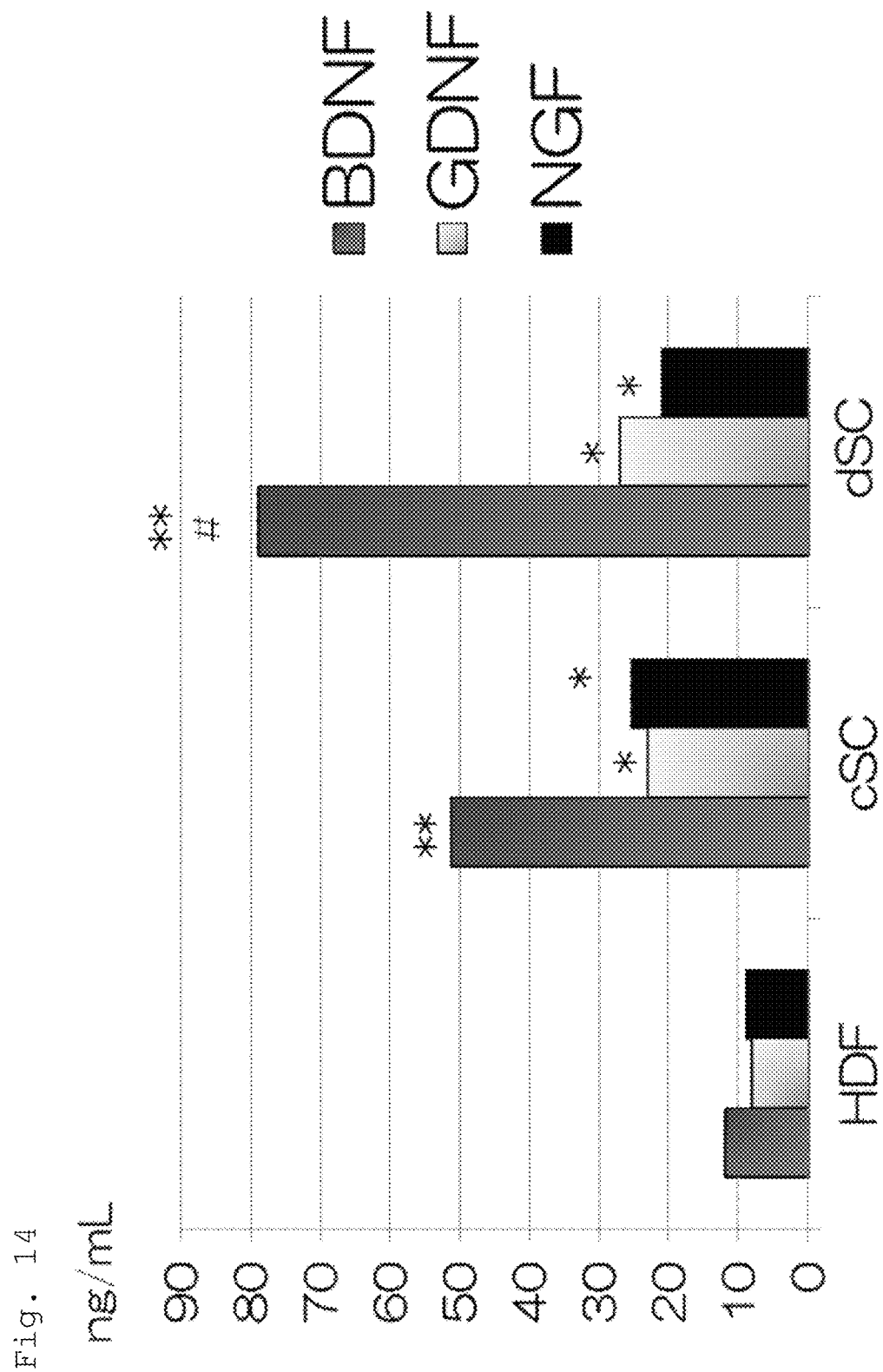

SCHWANN CELLS AND METHOD FOR PREPARING SAME

TECHNICAL FIELD

The present invention mainly relates to Schwann cells and a method for preparing them, more specifically a method for preparing Schwann cells by direct reprogramming.

BACKGROUND ART

Schwann cells are considered to play a critical role in nerve regeneration. There are many diseases associated with nerve defects and dysfunction of Schwann cells. If autologous Schwann cells can be transplanted, it is expected to be ideal regenerative medicine treatment for these diseases. In fact, treatment by autologous nerve grafting or by a method comprising separating Schwann cells from autologous nerves and culturing and transplanting the Schwann cells is effective for nerve damage due to external injury or removal of malignant tumors. However, harvesting of nerves is extremely invasive to patients, and secondary nerve damage is unavoidable. Further, the number of Schwann cells provided is often insufficient.

Non-patent Literature (NPL) 1 and 2 disclose a method for differentiating Schwann-cell-like cells (dADSC) by using mesenchymal stem cells, such as undifferentiated adipose-derived stem cells (ADSC) (also referred to as "adipose-derived stromal cells"), as a starting material. However, since this method inherently has a risk of external infection, quality control is not easy and the method is problematically costly and time-consuming. It has also been noted that the obtained cells are different from true Schwann cells in traits and functions. Further, Schwann cells created by these methods are not reported to have myelinating ability and may be unable to contribute to saltatory conduction.

Recent research shows that cardiomyocytes, hepatocytes, etc. can be directly induced from fibroblasts (direct reprogramming or direct conversion). If Schwann cells can be directly created from somatic cells, such as fibroblasts, which can be harvested from patients in a low-invasive manner, this will lead to a new low-invasive technique for creating autologous Schwann cells for transplantation with a low risk of oncogenesis.

The following, for example, has been reported regarding the technique of introducing a group of genes of tissue-specific transcription factors into somatic cells to induce direct differentiation into the intended tissue cells without passing through iPS cells (direct reprogramming (direct conversion)):
mouse fibroblasts→chondrocytes (introduction of SOX9+ Klf4+c-Myc genes);
mouse fibroblasts→cardiomyocyte (introduction of GATA4+Mef2c+Tbx5 genes);
mouse fibroblasts→hepatocytes (introduction of Hnf4α+ (Foxa1 or Foxa2 or Foxa3) genes);
mouse fibroblasts→neural stem cells (for example, introduction of Sox2+FoxG1 genes); and
mouse cells or human cells→hematopoietic stem cells; etc.

However, there have been no reports demonstrating direct conversion of somatic cells into Schwann cells.

CITATION LIST

Non-Patent Literature

NPL 1: Kingham P J, Kalbermatten D F, Mahay D, et al.: Adipose-derived stem cells differentiate into a Schwann cell phenotype and promote neurite outgrowth in vitro. Exp Neurol, 2007; 207: 267-274.
NPL 2: Liu Y, Zhang Z, Qin Y, Wu H, Lv Q, Chen X, Deng W: A new method for Schwann-like cell differentiation of adipose derived stem cells. Neurosci Lett. 2013 Sep. 13; 551: 79-83.

SUMMARY OF INVENTION

Technical Problem

An object of the present invention is to provide a method for preparing a Schwann cell that is applicable for the treatment of diseases associated with nerve defects and dysfunction of Schwann cells and that has a low risk of oncogenesis.

Solution to Problem

The present inventors found that introduction of a combination of specific genes into a somatic cell of a mammal can produce a Schwann cell directly (by direct reprogramming) without passing through pluripotent stem cells, such as embryonic stem (ES) cells or iPS cells.

The present invention includes the following inventions.
Item 1. A method for preparing a Schwann cell comprising introducing into a somatic cell of a mammal at least one gene selected from the group consisting of SOX10 and KROX20 genes, or an expression product thereof.
Item 2. The method according to Item 1, wherein the gene is a combination of SOX10 and KROX20 genes.
Item 3. The method according to Item 1 or 2, wherein the somatic cell is a fibroblast, a vascular endothelial cell, or a mesenchymal stem cell.
Item 4. A Schwann cell derived from a somatic cell of a mammal, the cell comprising at least one gene selected from the group consisting of exogenous SOX10 and KROX20 genes, or an expression product thereof.
Item 5. A grafting material for treating a disease based on a nerve defect, or a defect, deficiency, or hypofunction of Schwann cells, the grafting material comprising a cell obtained by the method according to any one of Items 1 to 3, or the Schwann cell according to Item 4.
Item 6. A composition for preparing a Schwann cell, the composition comprising at least one gene selected from the group consisting of SOX10 and KROX20 genes, or an expression product thereof.

Advantageous Effects of Invention

According to the present invention, Schwann cells can be prepared from somatic cells in a short period of time by direct reprogramming. Since the Schwann cells can be easily induced from somatic cells of a subject into which the Schwann cells are to be transplanted, immunological rejection or like problems do not arise in transplantation of the obtained Schwann cells. Further, Schwann cells can be directly induced from somatic cells without passing through iPS cells or ES cells, which avoids problems due to pluripotent stem cells, such as oncogenesis.

BRIEF DESCRIPTION OF DRAWINGS

FIG. 14 shows production of neurotrophic factors (neurotrophic factors: BDNF, GDNF, and NGF). Their production was measured by ELISA. *$p<0.05$ vs. control; **$p<0.01$ vs. control; #$p<0.05$ vs. cSC.

FIG. 2, FIG. 3, FIG. 4A, FIGS. 5A to 5D, FIG. 7A, FIG. 8, FIGS. 9A and 9B, FIGS. 10A and 10B, FIGS. 11A and 11B, and FIGS. 12B to 12C further include color-reversed images.

DESCRIPTION OF EMBODIMENTS

Figure 1:
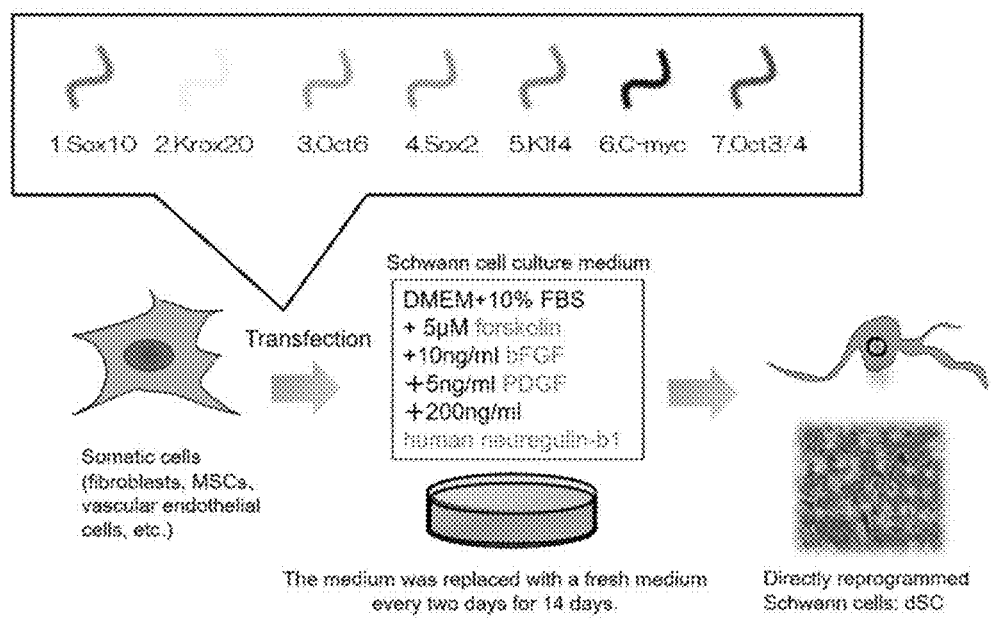
FIG. 1 outlines an example method of the present invention.

The present invention relates to a method for preparing Schwann cells. The preparation method of the present invention is a method for preparing Schwann cells without passing through pluripotent stem cells, such as embryonic stem (ES) cells or iPS cells.

Schwann Cells

Schwann cells are glial cells in the peripheral nervous system. Under physiological conditions, Schwann cells contribute to, for example, support of neural tissue and saltatory conduction by forming myelin (myelin sheath). When peripheral nerves are damaged, Schwann cells play many important roles in peripheral nerve regeneration, such as production and release of neurotrophic factors, scaffolding for regenerated axons, and myelinogenesis.

Unlike nerve cells directly derived from the ectoderm, natural Schwann cells are derived from the neural crest. Mature Schwann cells are formed through progenitor Schwann cells and immature Schwann cells. In this specification, for the sake of simplicity, all the cells during the differentiation process are included in the scope of "Schwann cells."

Schwann cells include Schwann cells that form myelin, migratory Schwann cells that do not form myelin (undifferentiated Schwann cells), and the like. In this specification, all of these Schwann cells are included within the scope of "Schwann cells."

In this specification, cells in which some or all of the functions are identifiable with those of natural Schwann cells, as well as cells that the same as natural Schwann cells, are called "Schwann cells."

Somatic Cells

Any somatic cells derived from a mammal can be used. Mammal-derived cells that are not Schwann cells or mammal-derived cells that have no ability to differentiate into Schwann cells in vivo are preferable. When Schwann cells are transplanted into a living subject, somatic cells derived from the subject into which the somatic cells are to be transplanted (autologous cells) are preferably used so as to reduce the risk of infection and rejection response, etc. However, when transplantation is performed due to sudden neural damage, Schwann cells prepared beforehand from somatic cells derived from other persons or other animals can be used for transplantation. Alternatively, Schwann cells can be produced from somatic cells of other persons or other animals, which were prepared beforehand, and can be used for transplantation. That is, a bank of Schwann cells (including a bank of Schwann cell progenitor cells) may be prepared and used for transplantation. In this case, to reduce the risk of, for example, rejection response, MHC can be typed beforehand. Further, cell characteristics, tumorigenicity, etc. of Schwann cells can be confirmed beforehand.

In this specification, examples of mammals include mice, rats, hamsters, humans, dogs, cats, monkeys, rabbits, cows, horses, pigs, and the like. Humans are particularly preferable.

The somatic cells to be subjected to the method of the present invention (direct reprogramming) are not particularly limited.

Somatic cells easily obtained from a biological organism can be used as the somatic cells. Examples include fibroblasts, keratinocytes, oral mucosal epithelial cells, nasal cavity mucosal epithelial cells, airway mucosal epithelial cells, gastric mucosal epithelial cells, intestinal mucosal epithelial cells, vascular endothelial cells, smooth muscle cells, adipocytes, gingival cells (gingival fibroblasts, gingival epithelial cells), dental pulp cells, periodontal membrane cells, marrow cells, marrow-derived stromal cells, leucocytes, lymphocytes, muscle cells, conjunctival epithelial cells, osteoclasts, and the like. Fibroblasts, keratinocytes, oral mucosal epithelial cells, gingival cells, leucocytes, lymphocytes, and the like are preferable. In the present invention, cells obtained from a biological organism are preferably used.

"Biological organism" or "living subject" used herein includes not only embryos (fetuses), larvae, juveniles, and adults, but also the placenta and umbilical cord that connect the mother and the fetus. Umbilical vascular endothelial cells and like umbilical-cord-derived cells and placenta-derived cells are not strictly considered to be somatic cells but these are also included in the scope of "somatic cells" of the present invention (in this case, the term "somatic cells" should be read as "umbilical vascular endothelial cells", "umbilical cord-derived cells", "placenta-derived cells", etc.). These cells are examples of somatic cells that are preferable from the viewpoint of ease of collection.

Examples of somatic cells also include somatic cells prepared from somatic stem cells, such as mesenchymal stem cells (MSCs), neural stem cells, hepatic stem cells, intestinal stem cells, skin stem cells, hair follicle stem cells, and melanocyte stem cells, by induction of differentiation, dedifferentiation, or reprogramming. Examples of somatic cells also include somatic cells prepared by inducing various somatic cells into other cells by induction of differentiation, dedifferentiation, or reprogramming. Examples of somatic cells also include somatic cells prepared from germ line cells by induction of differentiation, dedifferentiation, or reprogramming.

Examples of somatic cells also include somatic cells prepared from embryonic stem cells (ES cells) or induced pluripotent stem cells (iPS cells) by induction of differentiation or reprogramming.

In addition to the differentiated somatic cells, somatic stem cells can also be used. "Stem cells" as used herein refer to cells capable of self-replication or having ability to differentiate into other types of cells. Specific examples of such stem cells include mesenchymal stem cells (MSC) (such as adipose-derived stromal cells (ADSC), neural stem cells, hepatic stem cells, intestinal stem cells, skin stem cells, hair follicle stem cells, and melanocyte stem cells.

The "somatic cells" of the present invention also encompass ES cells, iPS cells, and germ line cells, although they are not, strictly speaking, somatic cells (in this case, the term "somatic cells" should be read as "ES cells," "iPS cells," or "germ line cells").

Examples of somatic cells also include cultured cells and somatic cells prepared from cultured cells by induction of differentiation, dedifferentiation, or reprogramming. Examples of somatic cells also include somatic cells prepared from ES cells, iPS cells, or germ line cells by induction of differentiation, dedifferentiation, or reprogramming.

In one preferable embodiment of the present invention, the somatic cells are fibroblasts, vascular endothelial cells (in particular, umbilical vascular endothelial cells) or mesenchymal stem cells (in particular, adipose-derived stromal cells).

Gene or Expression Product Thereof

In the method of the present invention, at least one gene selected from the group consisting of SOX10 and KROX20 genes or an expression product thereof is introduced into somatic cells. Examples of the "expression product" include mRNA and proteins expressed from SOX10 gene and/or KROX20 gene.

The usable gene combination includes SOX10 gene alone, KROX20 gene alone, and a combination of SOX10 and KROX20 genes. From the viewpoint of Schwann cell production efficiency, a combination of SOX10 and KROX20 genes is preferable.

In the method of the present invention, other genes can be used with at least one of SOX10 and KROX20 genes. microRNA, siRNA, shRNAm, or DNAs expressing these RNAs can also be used with SOX10 gene and/or KROX20 gene. Various proteins can also be used with SOX10 gene and/or KROX20 gene. SOX10 gene and/or KROX20 gene can be introduced with various other genes. It is preferable from the viewpoint of Schwann cell production efficiency and convenience that one or two genes, in particular, the two genes SOX10 and KROX20 alone are preferably used.

The SOX10 gene encodes a transcription factor that belongs to the SOX (SRY-related HMG-box) family and that is involved in controlling cell fate decisions in development of embryonic stages.

The KROX20 gene (also called "EGR2," "AT591," "CMT1D," or "CMT4E") encodes a protein having three C2H2-type zinc fingers.

The above genes are both highly conserved among vertebrates. The term "gene" herein includes its homologues unless the name of a particular animal is indicated. "Gene" also encompasses polymorphisms and mutated genes that have a function comparable to that of wild-type gene products.

For example, the cDNA nucleotide sequences of human (*Homo sapiens*) SOX10 and KROX20 genes and mouse (*Mus musculus*) SOX10 and KROX20 genes, as well as the amino acid sequences of proteins encoded by these sequences, have been registered at GenBank provided by the National Center for Biotechnology Information (NCBI), under the following accession numbers (it should be understood that when multiple revisions have been registered, each number refers to the latest revision):
Human SOX10 gene cDNA sequence: NM_00694 1 (for example, NM_006941.3);
Human SOX10 protein amino acid sequence: NP_008872 (for example, NP_008872.1);
Mouse Sox10 gene cDNA sequence: NM_011437 (for example, NM_011437.1);
Mouse SOX10 protein amino acid sequence: NP_035567 (for example, NP_035567.1);
Human KROX20 gene cDNA sequences: NM_000399, NM_001136177, NM_001136178, NM_001136179 (NM_000399.3, NM_001136177.1, NM_001136178.1, NM_001136179.1);
Human KROX20 protein amino acid sequences: NP_000390, NP_001129649, NP_001129650, NP_001129651 (for example, NP_000390.2, NP_001129649.1, NP_001129650.1, NP_001129651.1);
Mouse Krox20 gene cDNA sequence: NM_010118 (e.g., NM_010118.3) Mouse KROX20 protein amino acid sequence: NP_034248 (NP_034248.2).

Introduction

The method of the present invention can be performed in accordance with a known direct reprogramming method except that specific genes are selected and a medium suitable for Schwann cells is used. For example, the method can be performed according to the method described in any one of the following documents:
1: Direct Reprogramming of Fibroblasts into Functional Cardiomyocytes by Defined Factors; Masaki Ieda, Ji-Dong Fu, Paul Delgado-Olguin, Vasanth Vedantham, Yohei Hayashi, Benoit G. Bruneau, and Deepak Srivastava. Cell 142: 375-386, 2010.
2: Direct conversion of fibroblasts to functional neurons by defined factors. Thomas Vierbuchen, Austin Ostermeier, Zhiping P. Pang, Yuko Kokubu, Thomas C. Sudhof, and Marius Wernig. Nature 463: 1035-1041, 2010.
3: Induction of human neuronal cells by defined transcription factors. Pang Z P, Yang N, Vierbuchen T, Ostermeier A, Fuentes D R, Yang T Q, Citri A, Sebastiano V, Marro S, Sudhof T C, Wernig M. Nature 476: 220-223, 2011.
4: Generation of hyaline cartilaginous tissue from mouse adult dermal fibroblast culture by defined factors. Kunihiko Hiramatsu, Satoru Sasagawa, Hidetatsu Outani, Kanako Nakagawa, Hideki Yoshikawa, and Noriyuki Tsumaki. Journal of Clinical Investigation, 121: 640-657, 2011.
5: Induction of functional hepatocyte-like cells from mouse fibroblasts by defined factors. Pengyu Huang, Zhiying He, Shuyi Ji, Huawang Sun, Dao Xiang, Changcheng Liu, Yiping Hu, XinWang, and Lijian Hui, Nature 475: 386-389, 2011.
6: Direct conversion of mouse fibroblasts to hepatocyte-like cells by defined factors, Sayaka Sekiya, and Atsushi Suzuki. Nature 475: 390-393, 2011.
7: WO2014/010746

The contents of the above documents 1 to 7 are hereby incorporated by reference.

Specifically, it is preferable that a gene or genes of interest are incorporated into one or more expression vectors, the expression vectors are introduced into target somatic cells, and the genes are intracellularly expressed.

Examples of methods for introducing genes include a method of infection with viral vectors, such as retroviral vectors, adenoviral vectors, lentiviral vectors, adeno-associated viral vectors, herpes viral vectors, or Sendai virus vectors. When a gene or an expression product thereof is introduced, a method of transfection of a plasmid vector, an episomal vector, or an expression product of the gene (mRNA, protein) using a non-viral vector, such as a cationic liposome, a cationic polymer, or electroporation is also usable. mRNA can also be introduced. All the above gene transfer means are collectively referred to herein as "vectors."

Viral vectors are preferable in view of transfer efficiency and stable maintenance of transgenes. Plasmids are preferable in view of suppressing the risk of oncogenesis.

When a drug selection marker gene (conferring resistance to puromycin, blasticidin S, neomycin, hygromycin, etc.) is introduced with a gene of interest and then drug selection is performed, cells expressing the gene of interest can be selected and used.

The gene transfer of the present invention may be performed using a plasmid. Viral vectors, for example, retroviral vectors, may also be used. Viral vectors are preferable in view of transfer efficiency and stable maintenance of transgenes. Plasmids are preferable in view of suppressing the risk of oncogenesis.

The genes to be introduced into somatic cells can be transcribed by an LTR promoter, or may be expressed from another promoter inside the vector. For example, a constitutive expression promoter, such as a CMV promoter, EF-1α promoter, or CAG promoter, or a desired inducible promoter, may be used. Alternatively, a chimeric promoter in which a portion of LTR is replaced by another promoter may be used.

When an introduced factor is an expression product of a gene (for example, protein), the factor may be introduced into somatic cells by binding a peptide called a "protein transduction domain" (PTD) to the expression product protein, and adding the fusion protein to a culture medium.

In one embodiment of the method of the present invention, after a gene or the like is introduced into somatic cells, the cells into which the gene or the like has been transferred can be cultured in a medium suitable for culturing Schwann cells. The medium suitable for culturing Schwann cells may be a known medium. Examples of usable media include media (Schwann cell induction media) containing one or more of the following components (preferably all of the components) in a usual medium, such as a DMEM medium (Dulbecco's Modified Eagle's Medium) containing 10% FBS (fetal bovine serum): about 1 to 20 µM (particularly about 5 µM) forskolin; about 2 to 50 ng/ml (particularly 10 ng/ml about) bFGF (a basic fibroblast growth factor); about 2 to 50 ng/ml (particularly about 10 ng/ml) PDGF (platelet-derived growth factor); about 50 to 1000 ng/ml (particularly about 200 ng/ml) human neuregulin-β1 (also referred to as "heregulin" or "GGF" (glial growth factor)), etc.

The culture period is not particularly limited. For example, the culture period may be about 12 hours to about 1 month, about 1 day to about 3 weeks, or about 3 days to about 2 weeks. The medium can be replaced with a fresh medium, if necessary. The culture conditions are preferably in accordance with the usual method.

Preparation

Schwann cells are induced from somatic cells in this manner to obtain Schwann cells.

In one embodiment, the obtained Schwann cells have at least one gene selected from the group consisting of exogenous SOX10 and KROX20 genes, or expression product(s) thereof. The term "exogenous" as used herein means a gene or an expression product thereof that is introduced typically by the above introduction means and that is different from native genes or expression products thereof. Examples of exogenous genes include genes whose expression is controlled by a promoter other than native promoters, genes present at non-native chromosomal loci, extrachromosomal genes, and the like.

Production of Schwann cells can be confirmed, for example, by observation and evaluation of morphology (for example, the ratio of cell width to cell length); detection of expression of Schwann-cell-specific markers, such as S100β, p75NTR, GFAP, Nestin, and NG2 (e.g., detection of gene expression of a marker by RT-PCR, detection of expression of a marker protein by immunostaining, etc.); production of a neurotrophic factor; evaluation of neurite outgrowth effects on co-cultured neural cells, and functions as Schwann cells, such as myelinogenic capacity.

Schwann cells typically have a bipolar or multipolar cell morphology with a relatively small nucleus.

Among Schwann cell-specific markers, p75NTR is a marker of undifferentiated Schwann cells.

Myelinogenesis can be confirmed, for example, by detecting a myelin cell marker, such as myelin protein zero (MPZ, P0) or myelin basic protein (MBP), or observing myelin morphology.

Schwann cells may be obtained as a mixture of Schwann cells with other cells (such as original somatic cells). In such a case, Schwann cells can be separated from the cells other than Schwann cells, if necessary. The separation means is not particularly limited. For example, the separation of the obtained Schwann cells from fibroblasts, which are original cells, can be performed based on the difference in adhesion of cells to a scaffold (e.g., collagen). In general, Schwann cells are less adhesive to scaffolds than fibroblasts are. It is also possible to separate Schwann cells from other cells by sorting.

The Schwann cells prepared by the present invention can be suitably used, for example, as a grafting material described below.

The Schwann cells prepared by the present invention can be used, for example, for various research and technical developments. The Schwann cells are useful, for example, in basic research, such as analyzing the mechanisms of development, differentiation, and morphogenesis of Schwann cells, as well as analyzing the influences of dynamic stress, nutrition, hormones, etc. on development, differentiation, and morphogenesis of Schwann cells.

With the use of Schwann cells prepared by the present invention, Schwann cells can be established from humans or animals with various diseases or genetic backgrounds simply, rapidly, and inexpensively. Therefore, Schwann cell abnormalities associated with diseases or genetic backgrounds can be analyzed by a biochemical, molecular biological, immunological, or like method. Such analysis can aid in research such as elucidating pathogenesis of various diseases, and aid in the development of diagnostic methods. In addition, developing drugs, performing drug toxicity tests, etc. using such Schwann cells can contribute to the development of new therapies for various diseases.

Grafting Material

Schwann cells obtained by the present invention can be used for treating various diseases. In this case, Schwann cells can be provided in the foist of a grafting material.

The term "grafting material" refers to a material that comprises Schwann cells and is to be introduced into a biological organism for repairing and rebuilding nerve fibers. Schwann cells obtained by the present invention may be used for preparing a grafting material. The Schwann cells themselves can also be used as a grafting material. Accordingly, the Schwann cells may be transplanted into a patient as a cell preparation, or transplanted together with a substrate (scaffold) made of artificial material, or transplanted after Schwann cells and a scaffold are cultured together. The substrate (scaffold) functions, for example, as a nerve bridge. In these cases, the scaffold can be foisted into various three-dimensional shapes according to the transplantation purpose.

The grafting material of the present invention can be produced by a method comprising the Schwann cell preparation method described above.

Specific examples of the substrate (scaffold) include polyglycolic acid (PGA) tubes, collagen tubes, fibrin glues, polymeric foam tubes, gelatin tubes, tubes comprising a combination of polyglycolic acid (PGA) and collagen, and the like. Commercially available products, such as Nerve Bridge (produced by Toyobo Co., Ltd.), can also be used as tubes comprising a combination of polyglycolic acid (PGA) and collagen.

The grafting material can be used in accordance with autologous nerve grafting, or a therapeutic method comprising separating Schwann cells from autologous nerves and culturing and grafting the Schwann cells. Such a method is disclosed in the following documents:

1: Hadlock T, Sundback C, Hunter D, Cheney M, Vacanti J P. A polymer foam conduit seeded with Schwann cells promotes guided peripheral nerve regeneration. Tissue Eng 2000; 6: 119-127.
2: Jesuraj N J, Santosa K B, Macewan M R, Moore A M, Kasukurthi R, Ray W Z, Flagg E R, Hunter D A, Borschel G H, Johnson P J, Mackinnon S E, Sakiyama-Elbert S E. Schwann cells seeded in acellular nerve grafts improve functional recovery. Muscle Nerve. 2014 February; 49(2): 267-76.
3: Tabesh H, Amoabediny G, Nik N S, Heydari M, Yosefifard M, Siadat S O, Mottaghy K. The role of biodegradable engineered scaffolds seeded with Schwann cells for spinal cord regeneration. Neurochem Int. 2009 February; 54(2): 73-83.
4: Novikova L N, Pettersson J, Brohlin M, Wiberg M, Novikov L N. Biodegradable poly-beta-hydroxybutyrate scaffold seeded with Schwann cells to promote spinal cord repair. Biomaterials. 2008 March; 29(9): 1198-206.
5: Guest J, Santamaria A J, Benavides F D. Clinical translation of autologous Schwann cell transplantation for the treatment of spinal cord injury. Curr Opin Organ Transplant. 2013 December; 18(6): 682-9.
6: Brook G A, Lawrence J M, Shah B, Raisman G. Extrusion transplantation of Schwann cells into the adult rat thalamus induces directional host axon growth. Exp Neurol. 1994 March; 126(1): 31-43.
7: Vaudano E, Campbell G, Hunt S P. Change in the molecular phenotype of Schwann cells upon transplantation into the central nervous system: down-regulation of c-jun. Neuroscience. 1996 September; 74(2): 553-65.
8: Keirstead H S, Ben-Hur T, Rogister B, O'Leary M T, Dubois-Dalcq M, Blakemore W F. Polysialylated neural cell adhesion molecule-positive CNS precursors generate both oligodendrocytes and Schwann cells to remyelinate the CNS after transplantation, J Neurosci. 1999 Sep. 1; 19(17): 7529-36.
9: Wan H, An Y H, Sun M Z, Zhang Y Z, Wang Z C. Schwann cells transplantation promoted and the repair of brain stem injury in rats. Biomed Environ Sci. 2003 September; 16(3): 212-8.
10: Chen L, Fan X, Jin G, Wan X, Qiu R, Yi G, You Y, Xu Q. Treatment of rat with traumatic brain injury and MR tracing in vivo via combined transplantation of bone marrow stromal cells labeled with superparamagnetic iron oxide and Schwann cells, J Biomed Nanotechnol. 2014 February; 10(2): 205-15.
11: Shields S A, Blakemore W F, Franklin R J. Schwann cell remyelination is restricted to astrocyte-deficient areas after transplantation into demyelinated adult rat brain, J Neurosci Res. 2000 Jun. 1; 60(5): 571-8.

The contents of the above documents 1 to 11 are hereby incorporated by reference.

Examples of diseases to be treated include central neural defects or damage caused by cerebral infarction, spinal damage, or the like, and peripheral nerve defects or damage associated with damage, external injury, resection of tumors, or the like; diseases of the central nervous system, such as multiple sclerosis, neuromyelitis optica (Devic's syndrome), concentric sclerosis (Balo's disease), acute disseminated encephalomyelitis (ADEM), inflammatory diffuse sclerosis (Schilder's disease), infectious subacute sclerosing panencephalitis (SSPE), and progressive multifocal leucoencephalopathy (PML); diseases of the peripheral nervous system, such as Guillain-Barré syndrome, Miller Fisher syndrome, and chronic inflammatory demyelinating polyradiculoneuropathy; diseases based on Schwann cell defect, deficiency, or hypofunction, such as Charcot-Marie-Tooth disease (CMT); and the like.

Unless otherwise indicated, the term "treatment" as used herein means any treatment that is applied to a patient while the patient is suffering from a specific disease or disorder, and that can reduce the severity of the disease or disorder or one or more of the symptoms, or retard or slow the progression of the disease or disorder. The term "treatment" as used herein includes "prevention."

The Schwann cell obtained by the present invention can be used not only for the treatment of disease, but also for beauty and function enhancement. Any treatment provided to humans for beauty and function enhancement is also called "treatment" for reasons of convenience in the present specification. In this case, the term "patient" can be read as "healthy person" or "human", and the term "disease" can be read as "beauty" or "function".

The present invention can also be used in the treatment of disease not only for humans, but also for animals kept as pets such as dogs and cats, livestock such as cattle, horses, pigs, sheep, and chickens, and like mammals. In this case, the term "patient" should be read as "diseased livestock" or "mammal".

Composition

As described above, Schwann cells can be prepared by introducing into somatic cells at least one gene selected from the group consisting of SOX10 and KROX20 genes, or an expression product thereof. Accordingly, the present invention further provides a composition for preparing Schwann cells, the composition comprising at least one gene selected from the group consisting of SOX10 and KROX20 genes, or an expression product thereof. The composition for preparing the Schwann cells contains a factor used for inducing Schwann cells from somatic cells. The gene or expression product thereof is preferably contained in a form introducible into somatic cells. Examples of the form introducible into somatic cells include vectors in which the gene is incorporated. The above genes may be incorporated into separate vectors, or that two or more genes may be incorporated into one vector.

The types etc. of usable vectors are as described above.

Direct Reprogramming In Vivo

As described above, Schwann cells can be prepared by introducing into somatic cells at least one gene selected from the group consisting of SOX10 and KROX20 genes, or an expression product thereof.

When a nerve is damaged, fibroblasts are enriched at the damaged site. The enriched fibroblasts then form a fibrous scar.

Accordingly, when the preparation method of the present invention is applied, at least one gene selected from the group consisting of SOX10 and KROX20 genes, or an expression product thereof, is introduced into fibroblasts to induce Schwann cells at the damaged site by direct reprogramming, thus contributing to treatment of nerve damage and nerve regeneration. In the introduction of at least one gene selected from the group consisting of SOX10 and KROX20 genes, or an expression product thereof, the composition of the present invention can be suitably used.

It should be understood that the preparation method of the present invention includes direct reprogramming in vivo as described above, as well as direct reprogramming in vitro.

Direct reprogramming in vivo can be performed, for example, in accordance with direct reprogramming to cardiomyocytes in vivo as described in the following documents, except that at least one gene selected from the group consisting of SOX10 and KROX20 genes, or an expression product thereof, is introduced into fibroblasts at the damaged site of the nerve.

1: Ieda M. Heart regeneration using reprogramming technology. Proc Jpn Acad Ser B Phys Biol Sci. 2013; 89(3): 118-28. Review.
2: Ieda M, Fu J D, Delgado-Olguin P, Vedantham V, Hayashi Y, Bruneau B G, Srivastava D. Direct reprogramming of fibroblasts into functional cardiomyocytes by defined factors. Cell. 2010 Aug. 6; 142(3): 375-86.
3: Qian L, Huang Y, Spencer C I, Foley A, Vedantham V, Liu L, Conway S J, Fu J D, Srivastava D. In vivo reprogramming of murine cardiac fibroblasts into induced cardiomyocytes. Nature. 2012 May 31; 485(7400): 593-8.

The contents of the above documents 1 to 3 are hereby incorporated by reference.

EXAMPLES

The present invention is described below with reference to Examples. However, the scope of the invention is not limited to these Examples.

In the Examples, "HDF" refers to normal human dermal fibroblasts. "cSC" refers to control Schwann cells obtained from a living subject and cultured (cultured Schwann cells). "dSC" refers to Schwann cells obtained by the method of the present invention (directly reprogrammed Schwann cells). "Cont" refers to a control.

Example 1 Outline of the Method (FIG. 1)

FIG. 1 outlines a method for preparing Schwann cells according to the present invention ("directly reprogrammed Schwann cells: dSC" in FIG. 1).

The cDNA coding sequences of various genes, such as SOX10, were incorporated into pMXs-puro retroviral vector plasmids using a GeneArt system. Plat GP packaging cells were suspended in 1% NEAA 10% FBS DMEM (ordinary medium) containing 100 U/mL penicillin and 100 µg/mL streptomycin, and plated in gelatin-coated 10-cm culture dishes at a concentration of $5 \times 10^6$ cells/dish (day −3). After culturing for 24 hours, the pMXs vectors containing various genes were introduced in various combinations in the following proportion together with pCMV VSV vectors, using X-tremeGENE 9. More specifically, a mixture of 5 µg transgenes, 2.5 µg pCMV-VSV, 500 µl Opti-MEM, and 22.5 µl X-tremeGENE 9 was added to 10-cm dishes containing 10 ml of medium (day −2). After 24 hours, the medium was replaced with a antibiotic-free ordinary medium (day −1). On the same day (day −1), normal human dermal fibroblast line (aHDFs) ("fibroblasts" in FIG. 1) was plated on culture dishes or 12-well plates at $1.5 \times 10^4$ to $2 \times 10^4$ cells/mL. After 24 hours (day 0), the Plat GP culture supernatant was passed through a syringe filter with a pore diameter of 0.45 µm, and then mixed with polybrene (final concentration of 4 µg/mL) (virus suspension). After the culture supernatant of aHDFs was removed by suction, 1 mL of the virus suspension was quickly added, followed by culturing for 24 hours (infection; "Transfection" in FIG. 1). Non-virus-infected cells were prepared as a control group. One day later (day 1), the culture supernatant was removed by suction, and Schwann cell induction medium (medium obtained by adding 5 mM forskolin, 10 ng/ml recombinant human basic fibroblast growth factor (bFGF), 5 ng/ml recombinant human platelet-derived growth factor (PDGF), and 200 ng/ml recombinant heregulin 1-b1 (GGF)(all of these concentrations are final concentrations) to ordinary medium) was added. The medium was then replaced every two days with a fresh culture medium having the same composition. On day 12 to day 22, the obtained cells were stained for S100β, which is a representative Schwann cell marker. Cells that were cultured in the same manner but not infected with retroviral vectors were used as a control.

Figure 2:
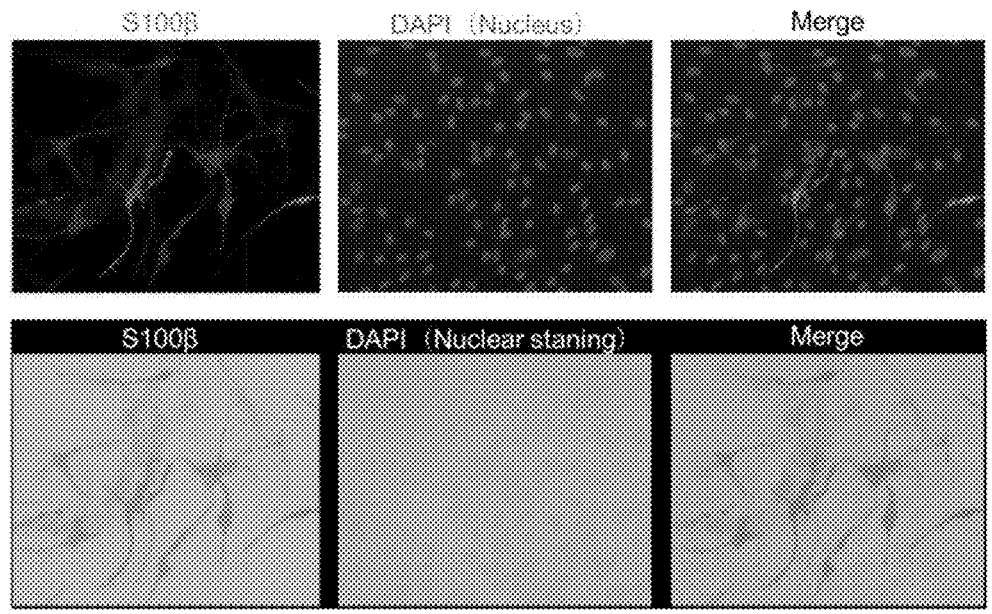
FIG. 2 shows typical S100β staining images.

Example 2 Conversion from Normal Human Dermal Fibroblasts into Schwann Cells, Fluorescent Immunostaining Images of S100β (FIG. 2)

Normal human dermal fibroblasts (aHDFs) were cultured in 12-well plates, and the same operation as in Example 1 was performed. On day 14, the culture medium was removed by suction from each well, and the cells were washed with PBS once and then fixed with 4% PFA. A blocking solution was added, and the plates were allowed to stand at 37° C. for 15 minutes. The cells were stained with an anti-S100β antibody (primary antibody) and an AlexaFluor566-conjugated anti-rabbit IgG antibody (secondary antibody). In each well of the plates, a different gene combination was introduced. Table 1 shows which gene combination was introduced into which numbered well (in the table, "1" means that the cells were infected with a retroviral vector containing the gene, whereas a blank means that the cells were not infected with a retroviral vector containing the gene). The introduced gene candidates were the following seven factors: SOX10, Krox20, and Oct6 as Schwann-cell-related genes and SOX2, C-myc, KLF4, and Oct3/4 as reprogramming-related genes. For example, No. 43 in Table 1 refers to cells infected with retroviral vectors containing SOX10, Krox20, Oct6, and KLF4 genes.

FIG. 2 shows, as typical S100β staining images, cells into which the two factors Sox10 and Krox20 genes were introduced. FIG. 2 shows co-staining with nucleus staining using DAPI (4′,6-diamidino-2-phenylindole).

Figure 3:
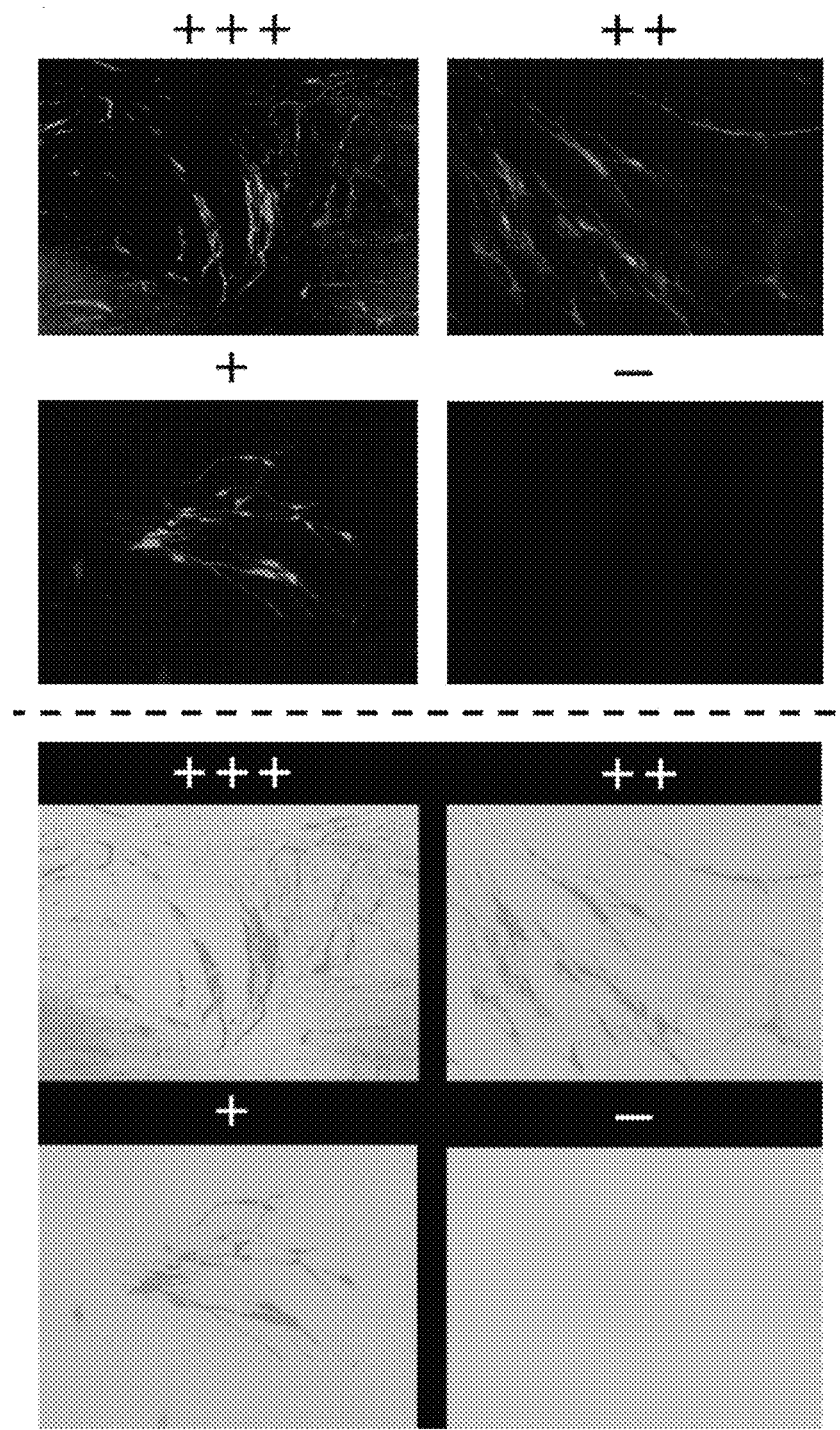
FIG. 3 shows a typical example of 4-point scale of S100β staining.

Example 3 Conversion from Normal Human Dermal Fibroblasts into Schwann Cells, Semi-Quantitation of S100β Staining (FIG. 3)

To confirm staining of other combinations in the same experiment as in FIG. 2, plates were observed under a fluorescence microscope (produced by Olympus Corporation) and S100β staining was evaluated on a 4-point scale (+++, ++, +, − in descending order from the greatest number of S100β-positive cells).

FIG. 3 shows typical images of each evaluation. Table 1 also shows the evaluation results. For example, No. 4 cells, which were infected with retroviral vectors containing both of SOX10 and KROX20 genes, were evaluated as +++ and shown to contain the largest number of S100β-positive cells. Although Schwann cells can be induced with low efficiency by introducing SOX10 alone or KROX20 alone, co-introduction of SOX10 and KROX20 can introduce Schwann cells with higher efficiency. The results show that Oct6 is almost completely ineffective in induction of Schwann cells.

Figure 4A:
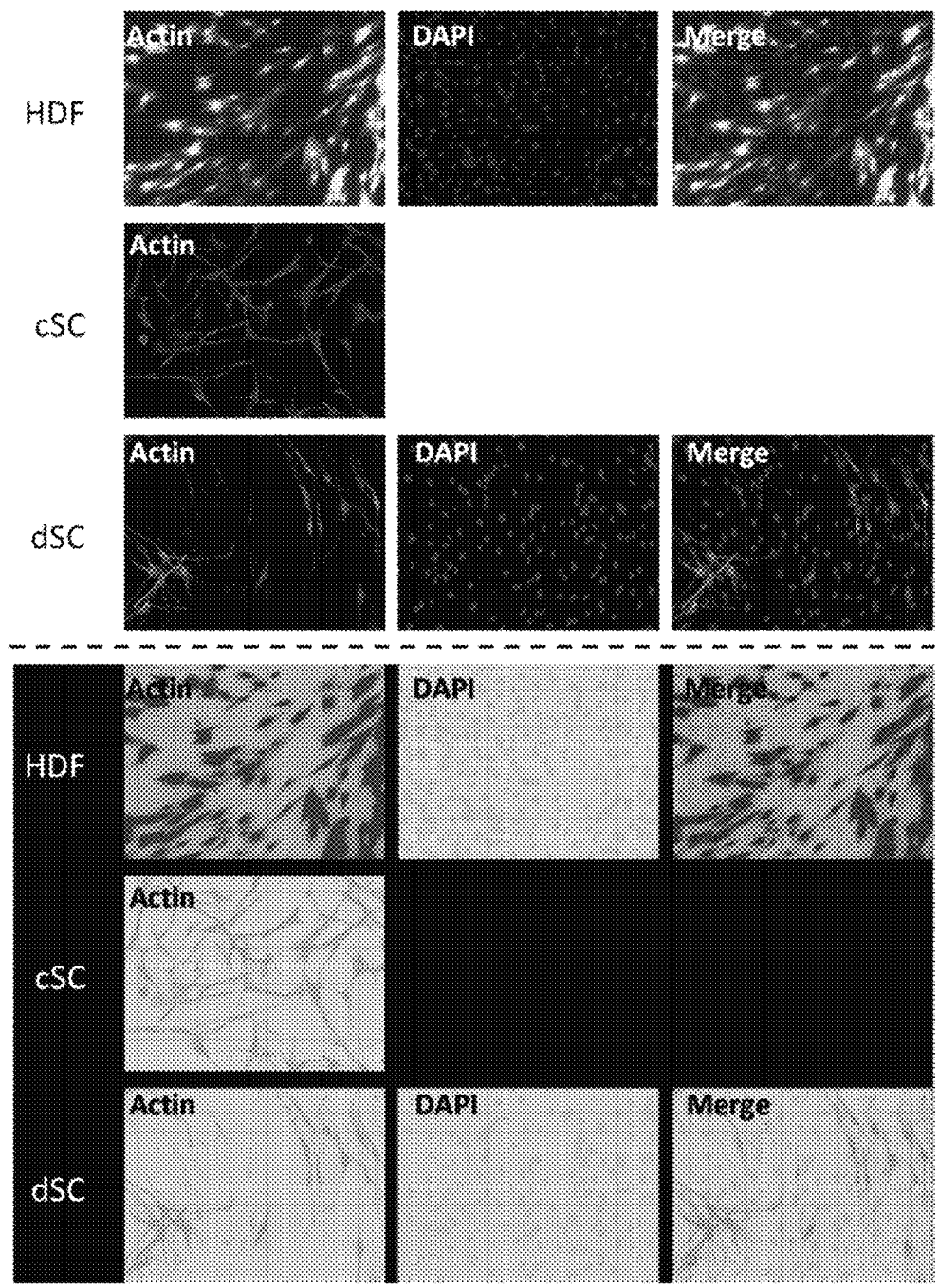
FIG. 4A shows the evaluation results in terms of cell morphology. Typical examples of cell morphology of HDF, cSC, and dSC are shown.
Figure 4B:
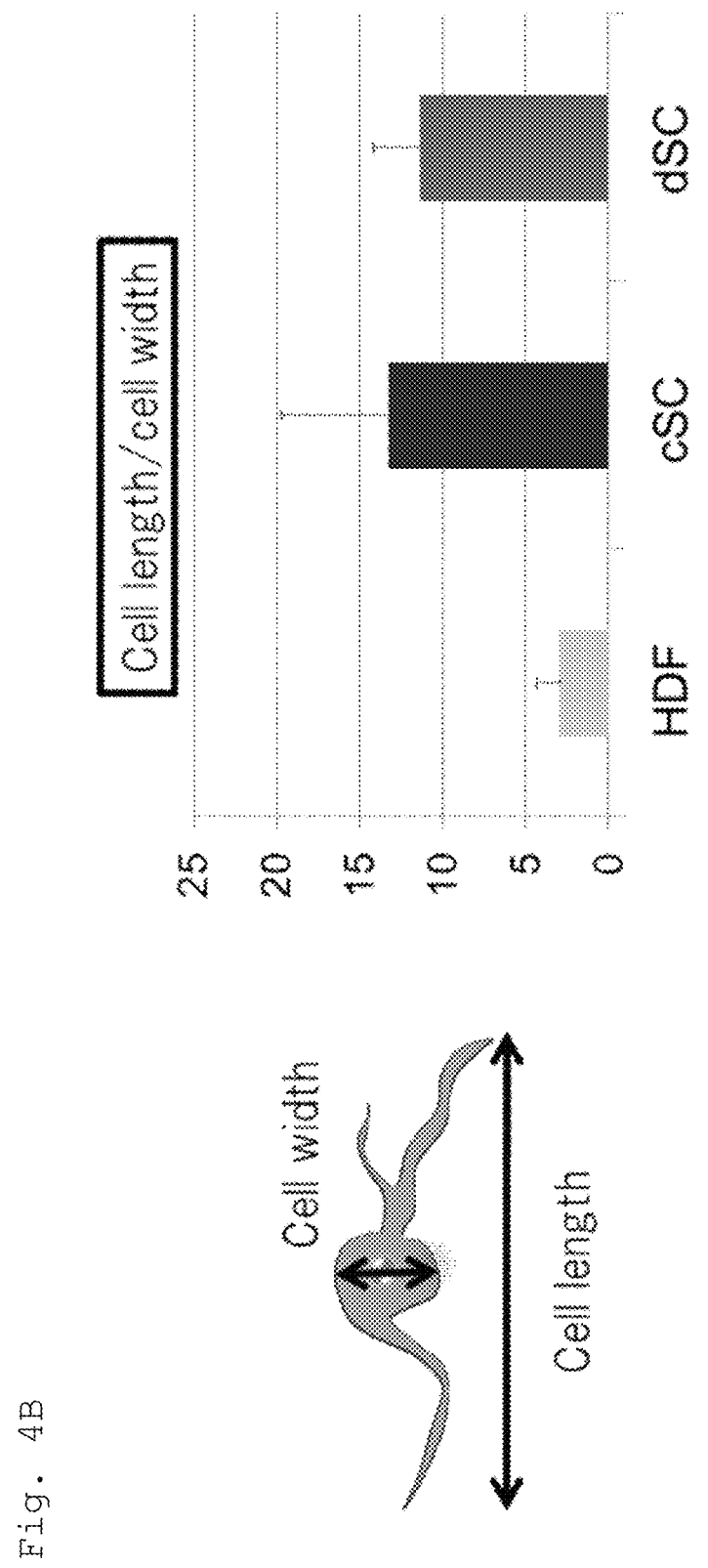
FIG. 4B shows the evaluation results in terms of cell morphology.
Figure 5A:
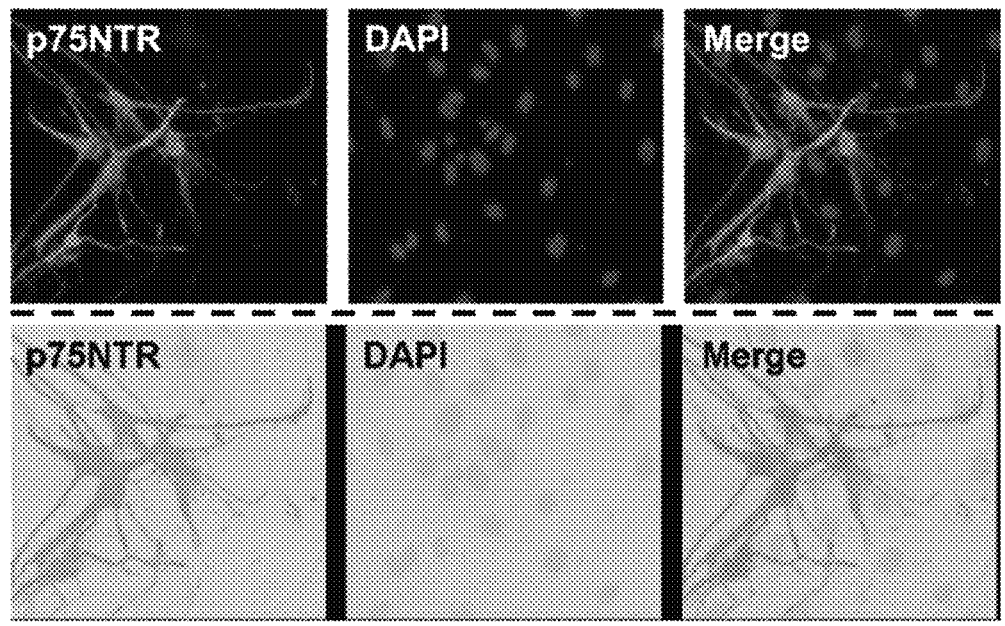
FIG. 5A shows an example of immunostaining of a Schwann-cell-related marker (p75NTR).
Figure 5B:
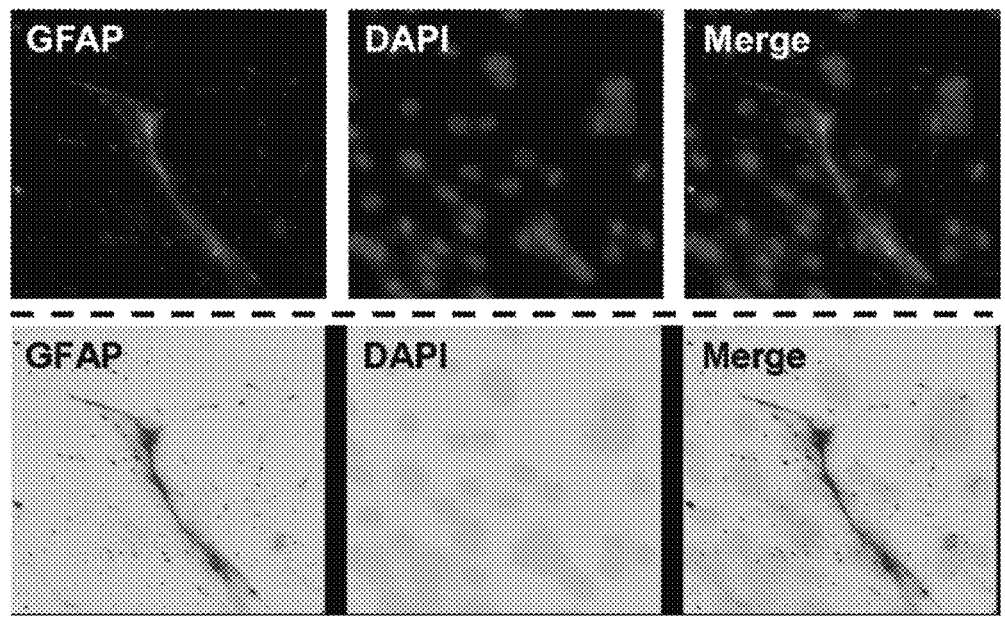
FIG. 5B shows an example of immunostaining of a Schwann cell-related marker (GFAP).
Figure 5C:
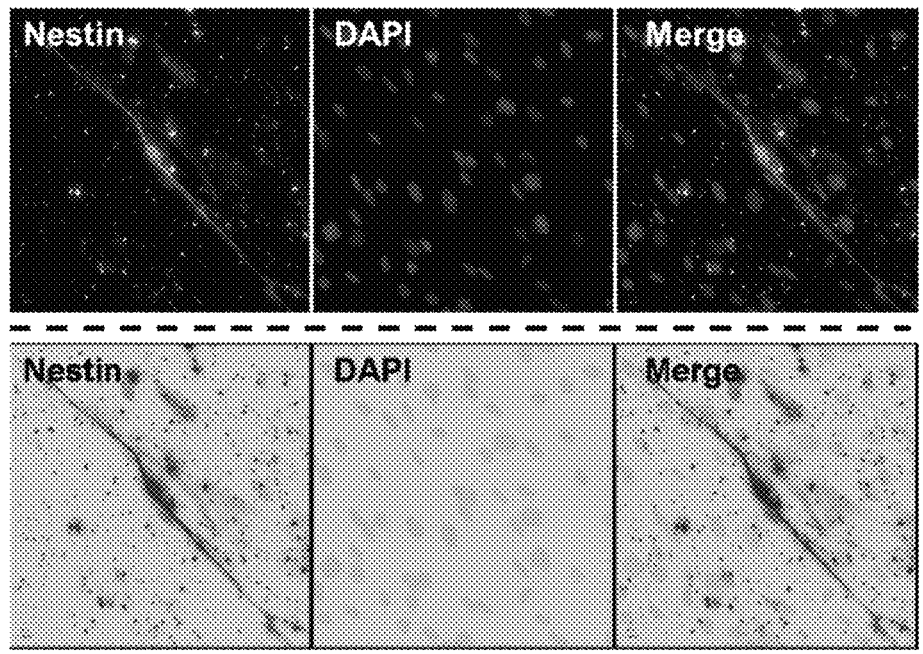
FIG. 5C shows an example of immunostaining of a Schwann cell-related marker (Nestin).
Figure 5D:
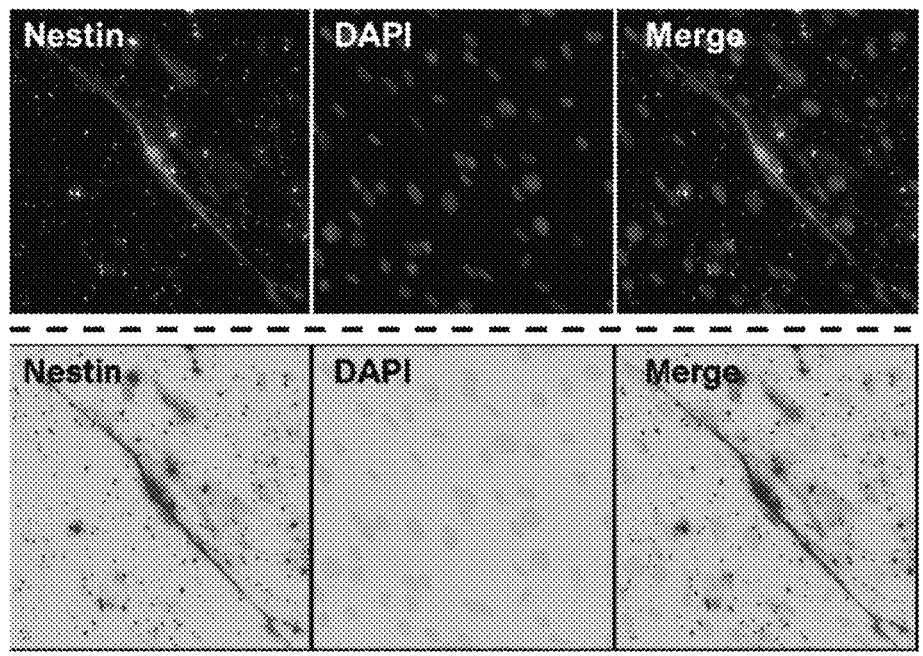
FIG. 5D shows an example of immunostaining of a Schwann cell-related marker (NG2).

Example 4 Conversion from Normal Human Dermal Fibroblasts into Schwann Cells, Cell Morphology Evaluation (FIG. 4)

Using the cells into which the genes of two factors Sox10 and Krox20 were introduced in Example 1, changes in cell morphology upon conversion of normal human dermal fibroblasts to Schwann cells were evaluated in terms of the ratio of cell length to cell width to determine the increase in bipolar cell length, which is a characteristic of Schwann cells.

TABLE 1

| | NO. 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| Evaluation | + | + | − | +++ | + | ++ | + | + | + | + | +++ | +++ | ++ | ++ | ++ | ++ | ++ | ++ |
| SOX10 | 1 | | | 1 | 1 | 1 | 1 | 1 | 1 | 1 | 1 | 1 | 1 | 1 | 1 | 1 | 1 | 1 |
| KROX20 | | 1 | | 1 | | 1 | | | | | 1 | 1 | 1 | 1 | 1 | 1 | 1 | 1 |
| OCT6 | | | 1 | | 1 | 1 | | | | | | | | | | | | |
| SOX2 | | | | | | | 1 | | | | 1 | | | | 1 | | | 1 |
| c-myc | | | | | | | | 1 | | 1 | | 1 | | | 1 | 1 | | |
| KLF4 | | | | | | | | | | | | | 1 | | | 1 | 1 | 1 |
| OCT3/4 | | | | | | | | | 1 | 1 | | | | 1 | | | 1 | |

| | NO. 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|
| Evaluation | + | ++ | ++ | ++ | +++ | ++ | ++ | + | + | + | + | + | + | + | + | + | + | + |
| SOX10 | 1 | 1 | 1 | 1 | 1 | 1 | 1 | 1 | 1 | 1 | 1 | 1 | 1 | 1 | 1 | 1 | 1 | 1 |
| KROX20 | 1 | 1 | 1 | 1 | 1 | 1 | 1 | | | | | | | | | | | |
| OCT6 | | | | | | | | 1 | 1 | 1 | 1 | | 1 | 1 | 1 | 1 | 1 | 1 |
| SOX2 | 1 | | 1 | 1 | 1 | | 1 | 1 | | | | 1 | | | 1 | 1 | | 1 |
| c-myc | | 1 | 1 | 1 | | 1 | 1 | | 1 | | | 1 | 1 | | | | 1 | 1 |
| KLF4 | | | 1 | | 1 | 1 | 1 | | | 1 | | | 1 | 1 | 1 | | | 1 |
| OCT3/4 | 1 | 1 | | 1 | 1 | 1 | | | | | 1 | | | 1 | | 1 | 1 | |

| | NO. 37 | 38 | 39 | 40 | 41 | 42 | 43 | 44 | 45 | 46 | 47 | 48 | 49 | 50 | 51 | 52 | 53 | 54 |
|---|---|---|---|---|---|---|---|---|---|---|---|---|---|---|---|---|---|---|
| Evaluation | + | + | + | + | ++ | ++ | + | ++ | + | + | + | + | ++ | ++ | + | ++ | + | + |
| SOX10 | 1 | 1 | 1 | 1 | 1 | 1 | 1 | 1 | 1 | 1 | 1 | 1 | 1 | 1 | 1 | 1 | 1 | 1 |
| KROX20 | | | | | 1 | 1 | 1 | 1 | 1 | 1 | 1 | 1 | 1 | 1 | 1 | 1 | 1 | 1 |
| OCT6 | 1 | 1 | 1 | 1 | 1 | 1 | 1 | 1 | 1 | 1 | 1 | 1 | 1 | 1 | 1 | 1 | 1 | 1 |
| SOX2 | 1 | 1 | | 1 | 1 | | | | 1 | | | 1 | 1 | | | 1 | 1 | |
| c-myc | 1 | | 1 | 1 | | 1 | | 1 | 1 | | | | 1 | 1 | | | | 1 |
| KLF4 | | 1 | 1 | 1 | | | 1 | | | 1 | 1 | 1 | | 1 | | | 1 | 1 |
| OCT3/4 | 1 | 1 | 1 | 1 | | | 1 | | | 1 | | | 1 | 1 | | 1 | 1 | 1 |

FIG. 4 shows the evaluation results. The results show that as a result of the conversion, the cell length/cell width ratio increases, i.e., the cell morphology changes to a morphology characteristic of Schwann cells.

Example 5 Conversion from Normal Human Dermal Fibroblasts into Schwann Cells, Fluorescent Immuno-Staining Images of Cells for Other Schwann-Cell-Related Markers (FIG. 5)

Normal human dermal fibroblasts aHDF were cultured in 12-well plates, and the same operation as in Example 1 was performed. The results of the group into which the two genes SOX10 and Krox20 were introduced are shown. Twelve days after the gene transfer, immunostaining was performed.

FIG. 5 shows the results. The hosts of anti-p75NTR antibody (primary antibody), anti-GFAP antibody (primary antibody), and anti-NG2 antibody (primary antibody) were rabbits. The hosts of anti-Nestin antibody (primary antibody) were mice. As a secondary antibody, AlexaFluor488, 566-conjugated anti-rabbit IgG antibody or AlexaFluor488-conjugated anti-mouse IgG antibody was used. Expression of each antigen was confirmed, although their positive rates were lower than that of S100β.

Example 6

A. Conversion from Normal Human Dermal Fibroblasts into Schwann Cells, Measurement of the mRNA Expression Level of S100β and p75NTR Genes (FIG. 6)

Normal human dermal fibroblasts (aHDFs) were cultured in 12-well plates, and the same operation as in Example 1 was performed. The genes of two factors Sox10 and Krox20 were introduced into cells in well Nos. 1 to 6, whereas no genes were introduced into cells in well Nos. 7 to 12 as controls. Twenty days after the gene transfer, total RNA was collected from each well using ISOGEN II, and cDNA was synthesized using a ReverTra Ace qPCR RT Master Mix. To determine the mRNA levels of UCP1 and β actin genes, Real-time PCR Master Mix, a TaqMan probe, specific primers, and cDNA were mixed, and real-time RT-PCR was performed using an AB7300 Real-Time PCR System. The mRNA levels of the genes of interest relative to the β-actin mRNA level of each well were calculated.

Figure 6:
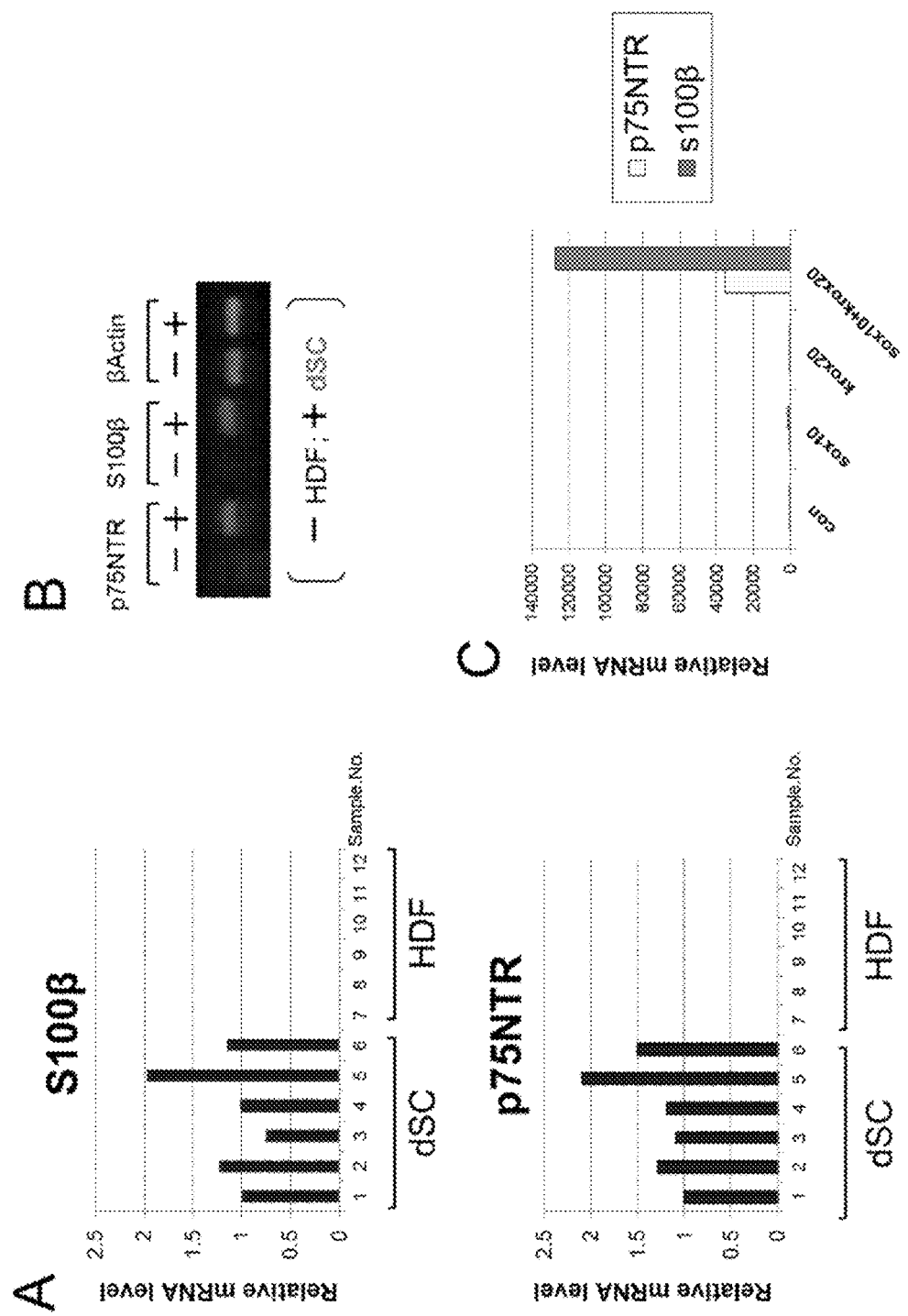
FIG. 6 shows the measurement results of mRNA expression levels of S100β and p75NTR genes.
Figure 7A:
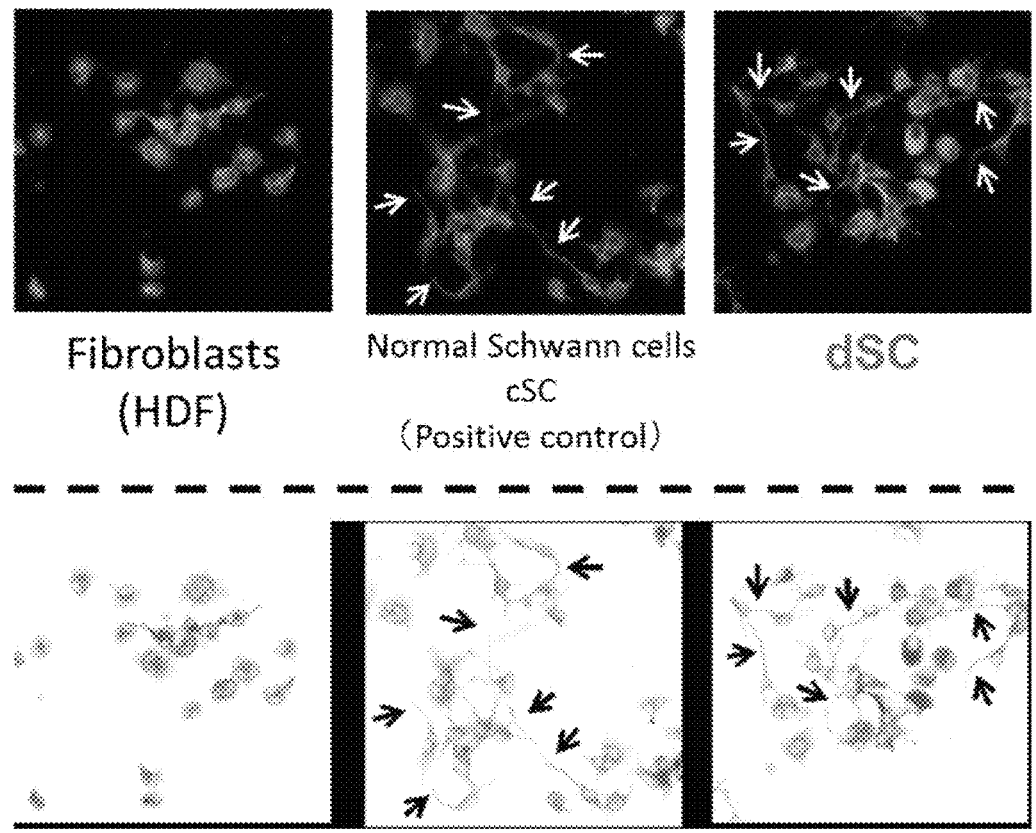
FIG. 7A shows the evaluation results of neurite outgrowth effects on nerve cells. An example of fluorescently labeled NG108-15 neurons co-cultured with fibroblasts HDF, normal Schwann cells (cSC, positive control), or dSC is shown. The arrows indicate extended neurites.
Figure 7B:
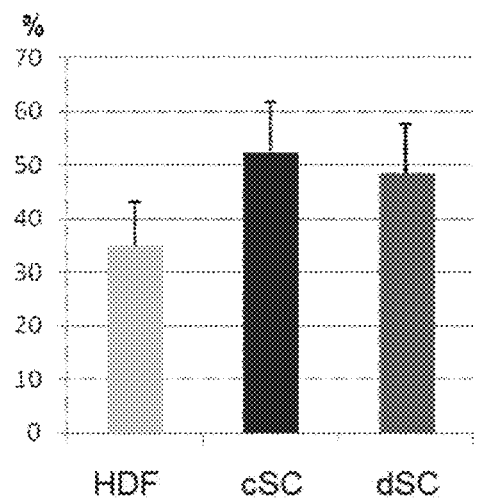
FIG. 7B shows the evaluation results of neurite outgrowth effects on nerve cells.
Figure 7B:
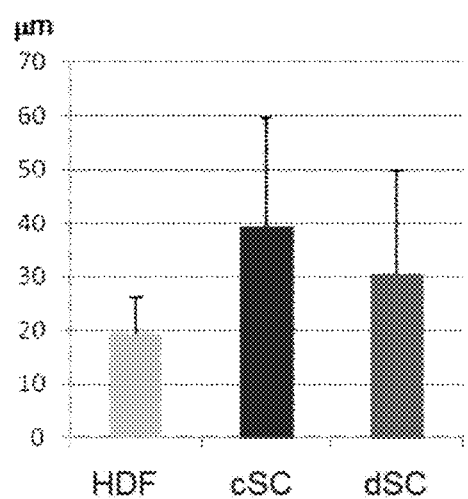
Figure 7B:
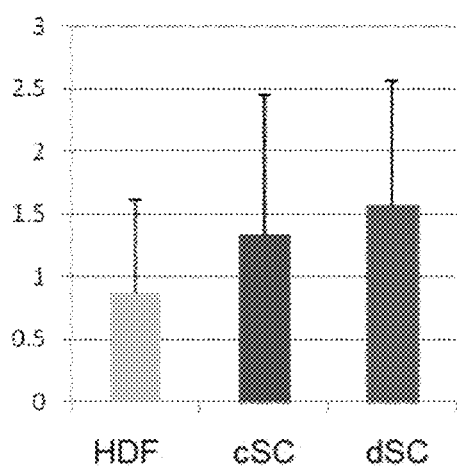

FIG. 6 shows the results. The vertical axis of the graph indicates relative values of each well that were calculated on the assumption that the value in well No. 1 was 1. Cells (Nos. 1 to 6) into which the two genes SOX10 and KROX20 were introduced exhibited strong expression of S100β and p75NTR genes, which are Schwann-cell-specific markers, compared to the controls (Nos. 7 to 12).

B. Electrophoresis Using Agarose Gel of RT-PCR Product

The real-time RT-PCR product obtained in A was subjected to electrophoresis using an agarose gel. As a result, strong expression of mRNA of S100β and p75NTR genes was confirmed in the cell group into which the genes of two factors SOX10 and Krox20 were introduced.

C. Analysis of Direct Reprogramming Efficiency from Human Fibroblasts into Schwann Cells by Introducing No Factors, Introducing SOX10 Alone, Introducing Krox20 Alone, or Introducing a Combination of SOX10 and Krox20

Normal human dermal fibroblasts aHDFs were cultured in 12-well plates, and the same procedure as in Example 1 was performed. The mRNA expression of S100β and p75 NTR in the following cells was compared in the same manner as in A: cells into which no genes were introduced (control); cells into which only SOX10 gene was introduced; cells into which only Krox20 gene was introduced; and cells into which SOX10 and Krox20 genes were introduced. Relative mRNA values are shown as relative mRNA levels. The mRNA level of the gene of interest relative to the β actin mRNA level in each group was calculated. With the mRNA level in a cell group into which no genes were introduced being defined as "1," the average of the relative values calculated in each group was shown as a relative mRNA level. As a result, in the group into which the two factors SOX10 and Krox20 were introduced, the mRNA expression levels of S100β and p75NTR increased greatly. The mRNA expression levels of S100β and p75NTR increased even in the cells into which only Sox10 was introduced, although the increase was lower than the increase in the cells into which both Sox10 and Krox20 were introduced. The mRNA expression level of S100β increased even in the cells into which only Krox20 was introduced, although the increase was lower than the increase in the cells into which both Sox10 and Krox20 were introduced. The relative mRNA level of S100β was 4.4 in the cells into which no genes were introduced, 1712.3 in the cells into which only Sox10 was introduced, 25.1 in the cells into which only Krox20 was introduced, and 127615.0 in the cells into which Sox10 and Krox20 were introduced. The relative mRNA level of p75NTR was 3.1 in the cells into which no genes were introduced, 74.3 in the cells into which only Sox10 was introduced, 0.4 in the cells into which only Krox20 was introduced, and 35397.6 in cells into which Sox10 and Krox20 were introduced. Thus, direct reprogramming of human fibroblasts into Schwann cells may occur with low efficiency by introduction of SOX10 or Krox20 alone.

The above results confirmed that direct reprogramming from human fibroblasts into Schwann cells occurs with high efficiency when the two factors SOX10 and Krox20 are used. Further, the results show that even when one factor, either SOX10 or Krox20, is used, direct reprogramming from human fibroblasts into Schwann cells is possible, although the efficiency is low.

Example 7 Analysis of Neurite Outgrowth Effects of dSC on Nerve Cells (FIG. 7)

NG108-15 was cultured for 12 hours and then co-cultured with HDF, cSC, or dSC (dSC induced by introducing the genes of two factors Sox10 and Krox20) for 36 hours. As a control, NG108-15 was cultured in 1% FBS-containing DMEM alone. The resulting cells were compared and analyzed in terms of the parameters: I. percent of neurite-bearing cells; II. number of primary neurites directly extend from cell bodies; and III. longest neurite length, by the methods described in the following document: Tomita K, Madura T, Sakai Y, et al: Glialdifferentiation of human adipose-derived stem cells: implications for cell-based transplantation therapy. Neuroscience. 2013; 236: 55-65. NG108-15 alone was fluorescently stained using Anti-Tuj-1 antibody (as primary antibody) and AlexaFluor566-conjugated anti-rabbit IgG antibody as a second antibody.

FIG. 7 shows the results. Compared to the control group, cSC and dSC both exhibited high neurite outgrowth-promoting effects in all the parameters (I to III). The results of dSC were comparable to those of cSC. The above results confirmed that the dSC culture supernatant promotes neurite outgrowth of nerve cells.

Figure 8:
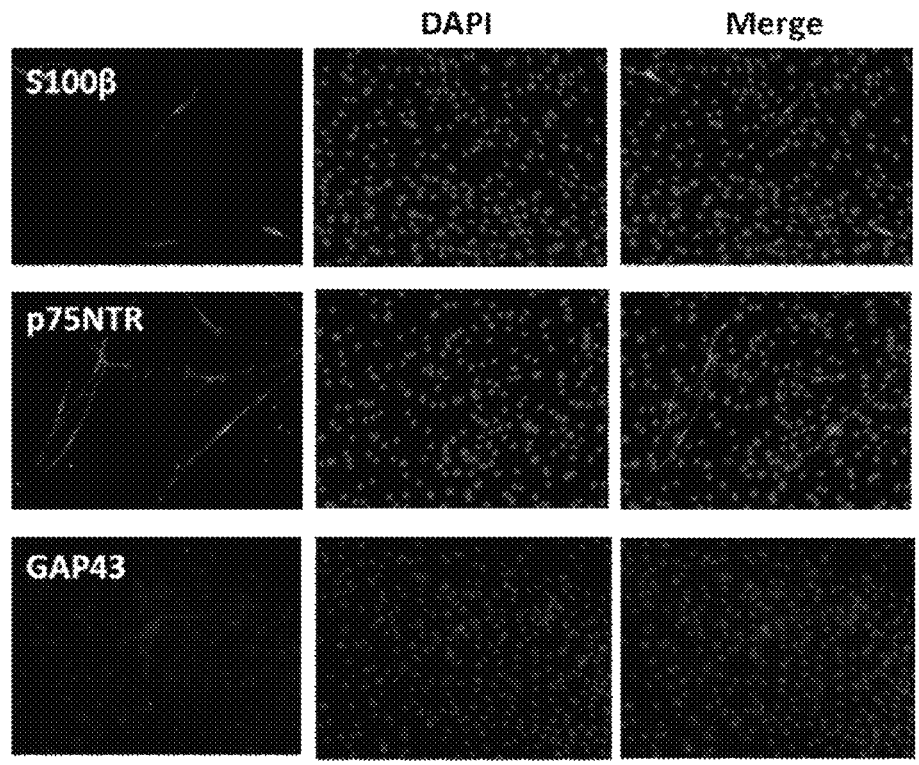
FIG. 8 shows an example of immunostaining of Schwann-cell-related markers (S100β, p75 NTR, and GAP43) in cell conversion experiments induced by plasmid transfection (electroporation).
Figure 8:
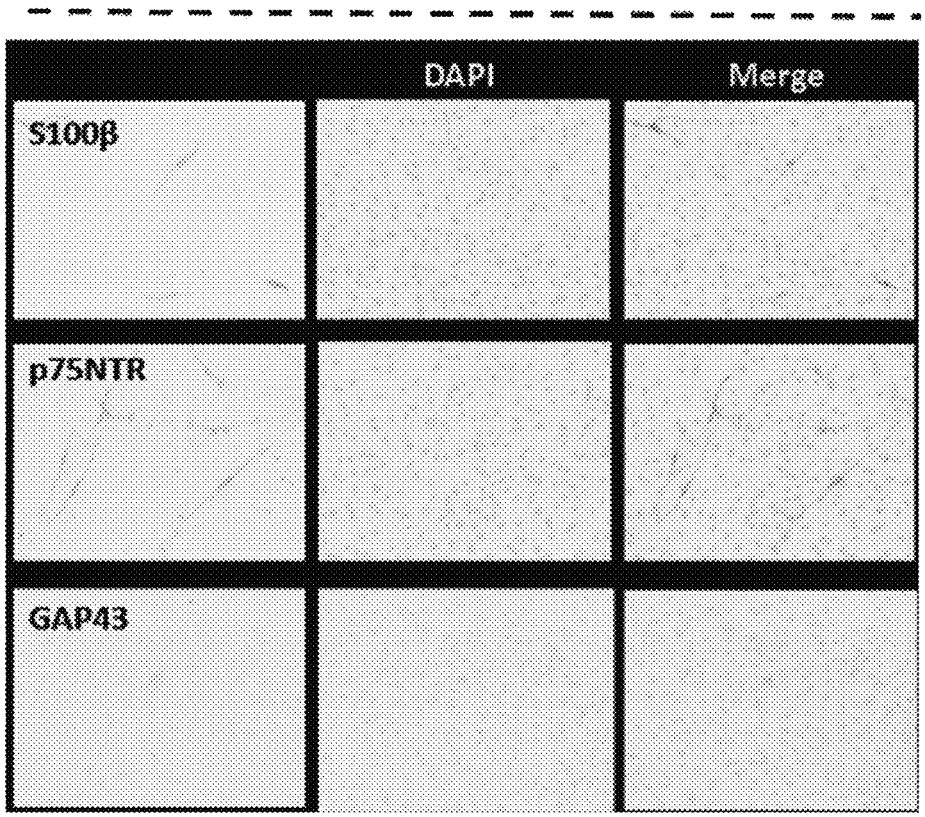

Example 8 Conversion from Normal Human Dermal Fibroblasts into Schwann Cells by Virus-Free Plasmid Introduction (Electroporation) (FIG. 8)

Normal human dermal fibroblasts aHDFs were cultured in 12-well plates, and the same procedure as in Example 1 was performed. FIG. 8 shows the results of a group into which the two genes SOX10 and Krox20 were introduced. Fourteen days after the gene transfer, immunostaining was performed.

FIG. 8 shows the results. The hosts of anti-S100β antibody (primary antibody), anti-p75NTR antibody (primary antibody), and anti-GAP43 antibody (primary antibody) were rabbits. As a secondary antibody, AlexaFluor566-conjugated anti-rabbit IgG antibody was used. Expression of S100β, p75 NTR, and GAP43 was confirmed, although their positive rates were low, compared with the case of using retroviral vectors. The conversion from fibroblasts aHDF into Schwann cells was confirmed.

Example 9 Conversion from Normal Human Adipose-Derived Stem Cells into Schwann Cells, Immuno-Fluorescent Staining Image of Cells for Other Schwann Cells-Related Markers (FIG. 9)

The conversion from adipose-derived stromal cells into dSC was analyzed.
Method
Normal human adipose-derived stromal cells (ADSC) were cultured in 12-well plates, and the same procedure as in Example 1 was performed. The results of the group into which the two genes SOX10 and Krox20 were introduced are shown. Fourteen days after the gene transfer, immunostaining was performed.
Result
FIG. 9 shows the results. The hosts of anti-S100β antibody (primary antibody), anti-p75NTR antibody (primary antibody), anti-GAP43 antibody (primary antibody), and anti-protein zero antibody (primary antibody) were rabbits. As a secondary antibody, AlexaFluor566-conjugated anti-rabbit IgG antibody was used. In staining for S100β, about 40% of the cells were positive. Expression of other Schwann cells markers was confirmed although their positive rates were lower than that of S100β. The cells were also positive for the myelin marker protein zero.

Figure 9A:
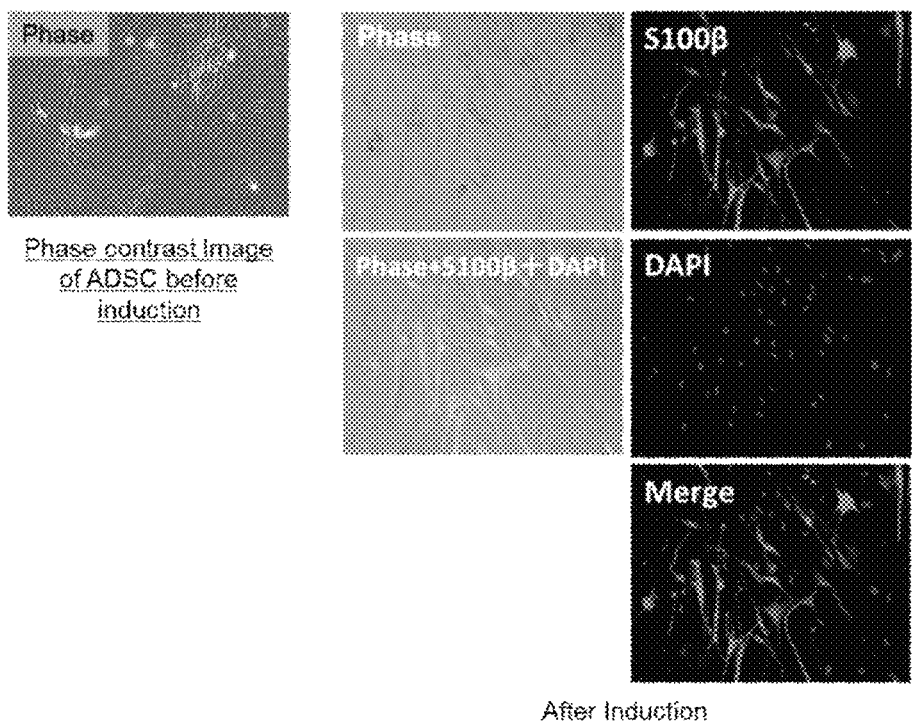
FIG. 9A shows phase contrast images of normal human adipose-derived stem cells (ADSC) before induction and their phase contrast images after induction to Schwann cells, and S100β staining images. The magnification is ×200.
Figure 9A:
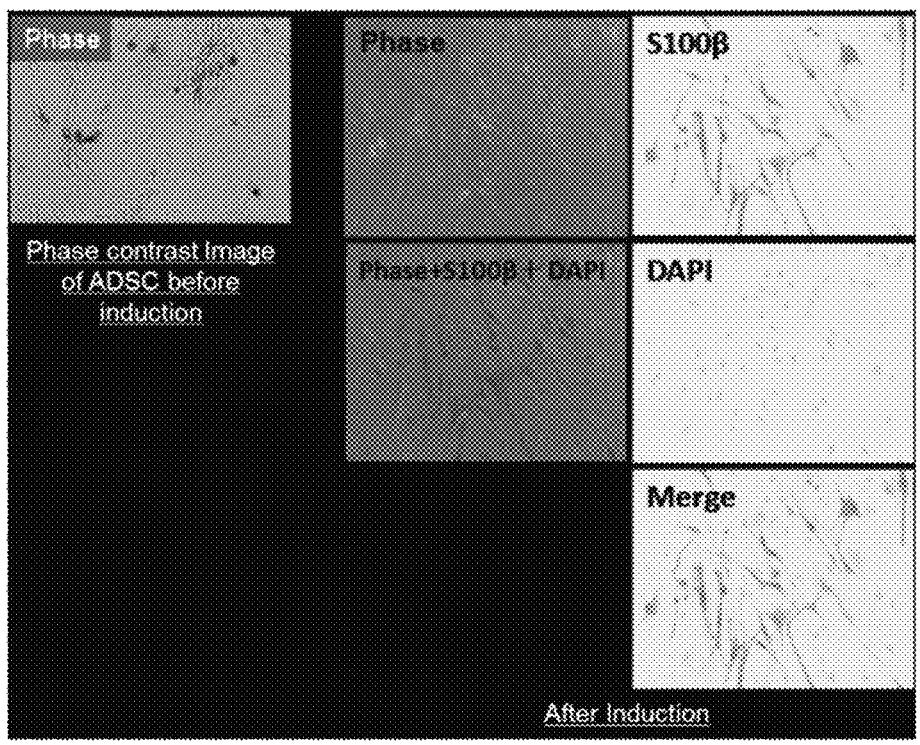

Specifically, normal human adipose-derived stromal cells were induced into Schwann cells in the same manner as induction from fibroblasts. The cell morphology changed from the morphology of normal human adipose-derived stromal cells to a bipolar or multipolar cell morphology having a relatively small nucleus, which is typical of Schwann cells. Further, the cells that changed to a cell morphology typical of Schwann cells were positive for a Schwann cell marker (S100β) (about 40 to 50%) (FIG. 9A).

Figure 9B:
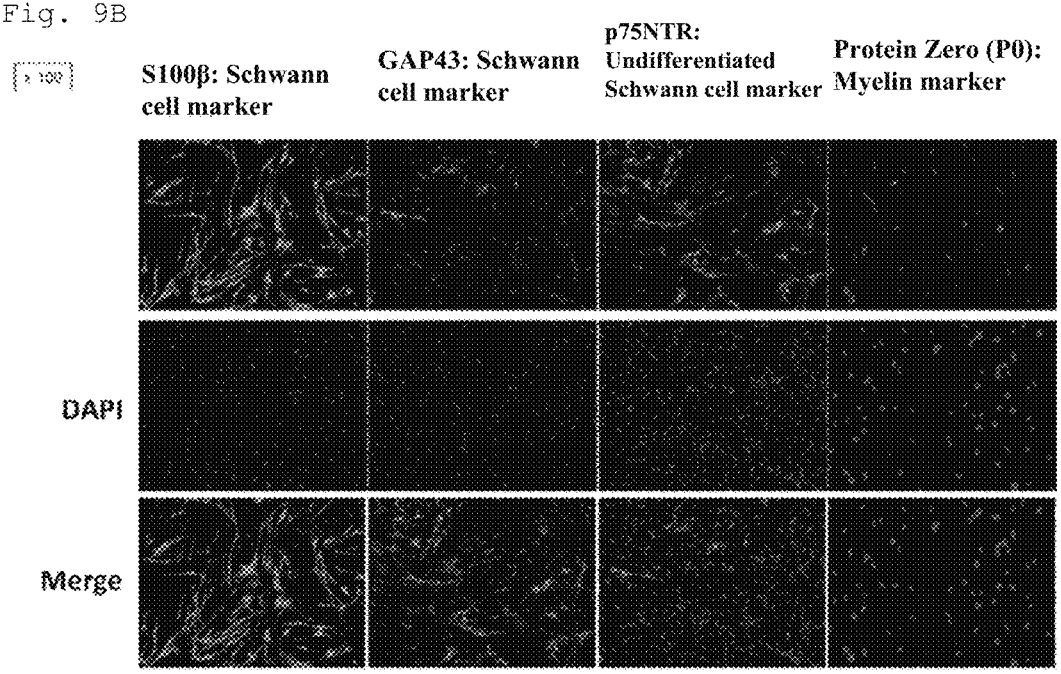
FIG. 9B shows an example of immunostaining of Schwann-cell-related markers (S100β, GAP43, p75NTR, and Protein Zero (PO)). The magnification is ×100.
Figure 9B:
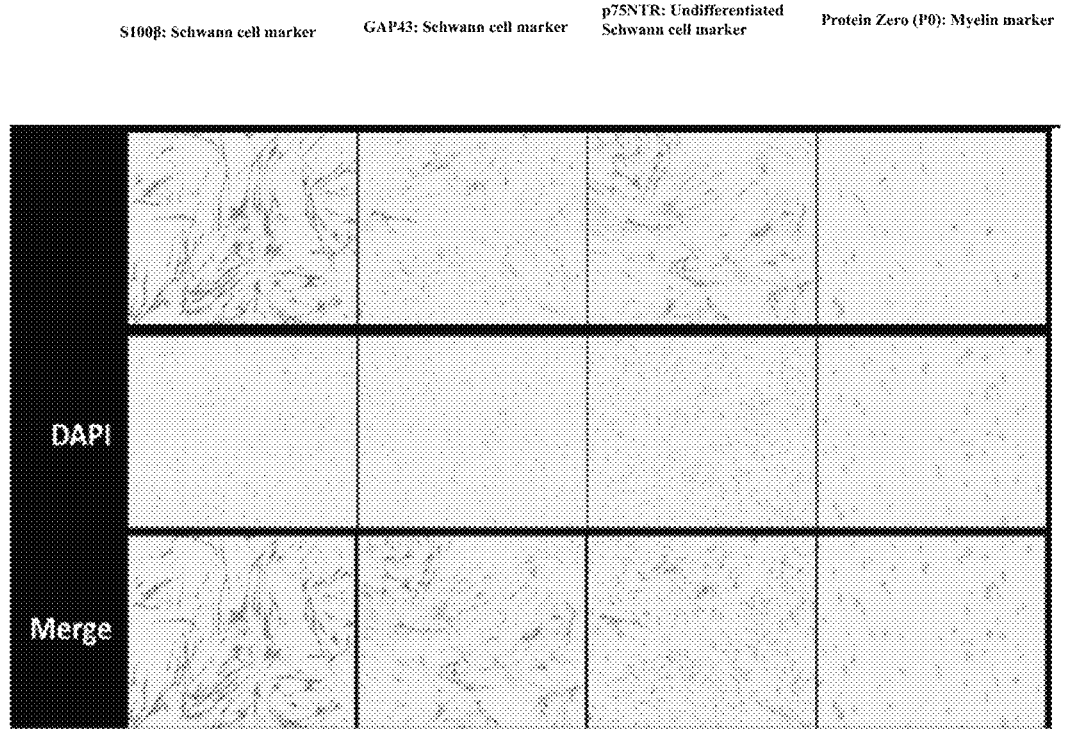

The cells after induction were positive for Schwann cell markers (S100β, GAP43), an undifferentiated Schwann cell marker (p75NTR), and a myelin marker (P0) (FIG. 9B).

Example 10 Conversion from Umbilical Vascular Endothelial Cells into Schwann Cells, Immuno-Fluorescent Staining Images of Cells for Other Schwann-Cell-Related Markers (FIG. 10)

The conversion from vascular endothelial cells into dSC was examined.
Method
Human umbilical vascular endothelial cells (Huvec) were cultured in 12-well plates, and the same operation as in Example 1 was performed. The results of a group into which the two genes SOX10 and Krox20 were introduced are shown. Fourteen days after the gene transfer, immunostaining was performed.
Results
FIG. 10 shows the results. The hosts of anti-S100β antibody (primary antibody), anti-p75NTR antibody (primary antibody), anti-GAP43 antibody (primary antibody), and anti-protein zero antibody (primary antibody) were rabbits. As a secondary antibody, 566-conjugated anti-rabbit IgG antibody was used. In staining for S100β, about 30% of cells were positive. Expression of other Schwann cells markers was also confirmed, although their positive rates were lower than that of S100β. The cells were also positive for the myelin marker protein zero.

Figure 10A:
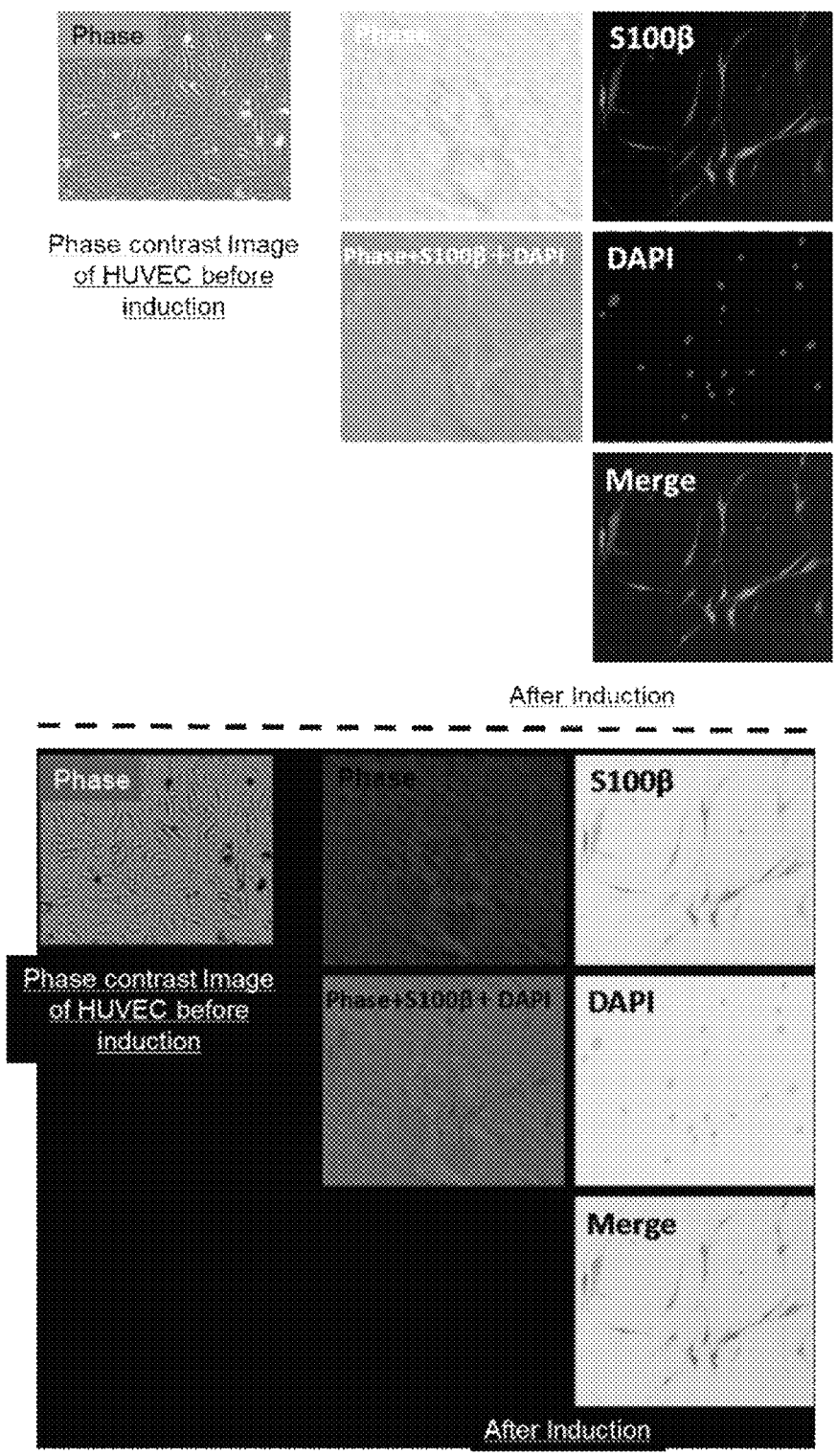
FIG. 10A shows phase contrast images of umbilical vascular endothelial cells (Huvec) before induction, their phase contrast images after induction to Schwann cells, and S100β staining images. The magnification is ×200.

Specifically, human umbilical vascular endothelial cells were induced into Schwann cells in the same manner as induction from fibroblasts. The cell morphology changed from the morphology of umbilical vascular endothelial cells to a bipolar or multipolar cell morphology having a relatively small nucleus, which is typical of Schwann cells. Further, the cells that changed to a cell morphology typical of Schwann cells were positive for a Schwann cell marker (S100β) (about 50 to 60%) (FIG. 10A).

Figure 10B:
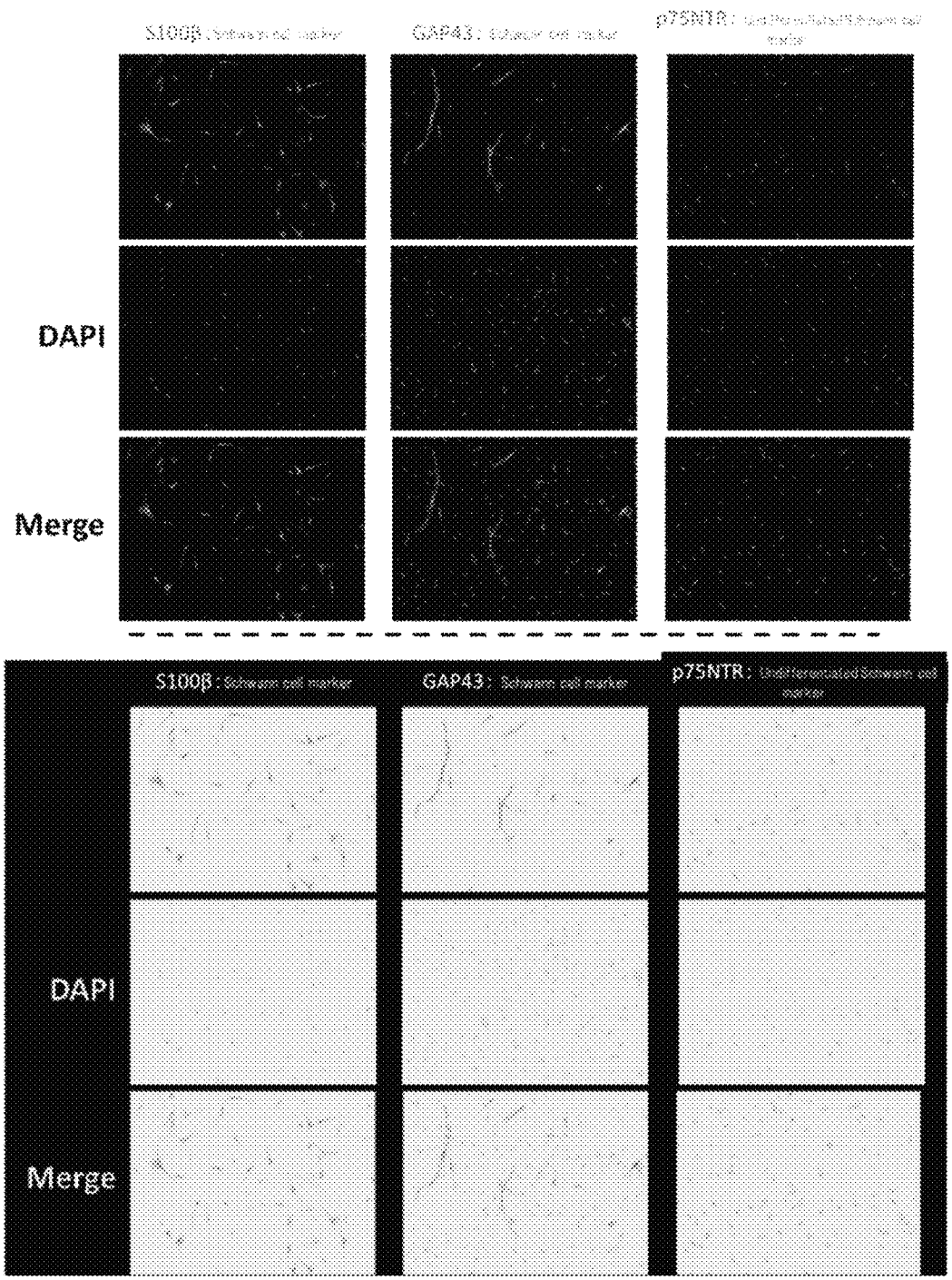
FIG. 10B shows an example of immunostaining images of Schwann-cell-related markers (S100β, GAP43, and p75NTR). The magnification is ×100.
Figure 11A:
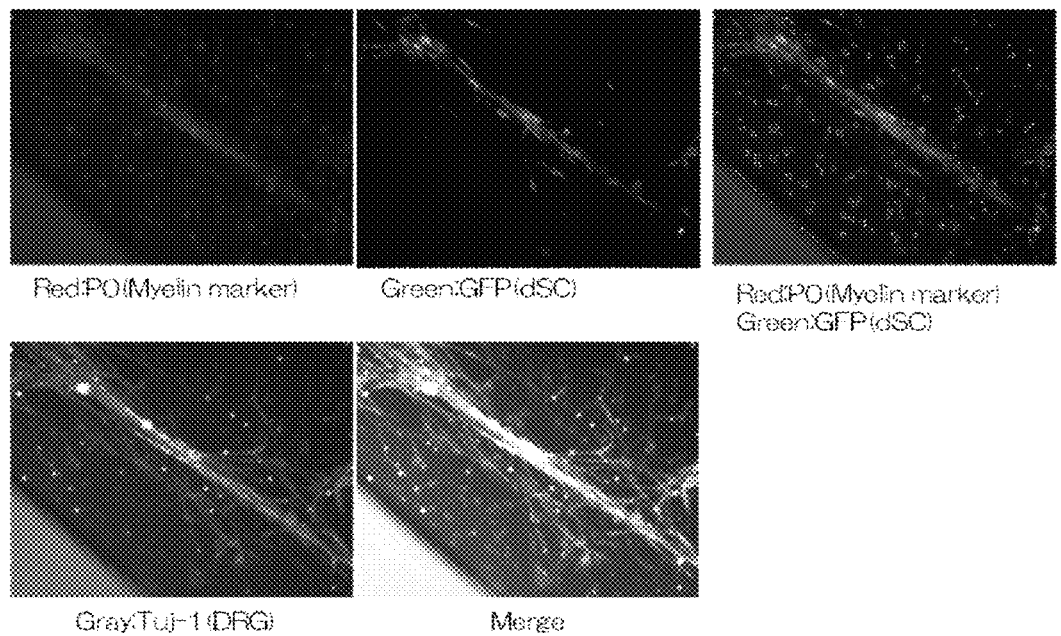
FIG. 11A shows an example of immunostaining images of a myelin marker (protein zero (P0)).
Figure 11A:
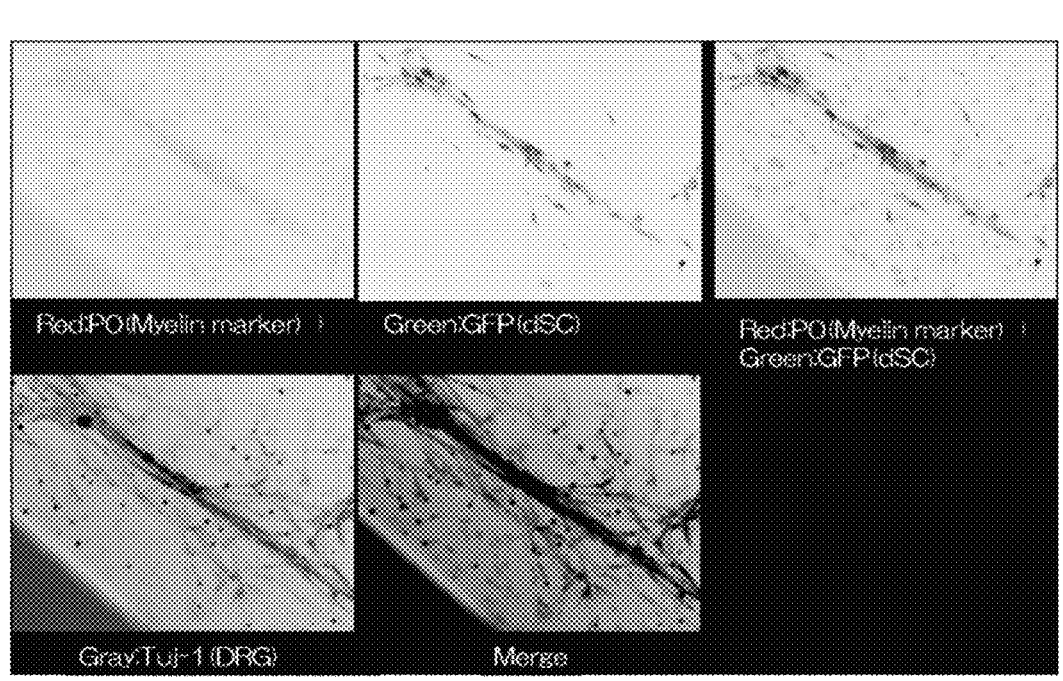
Figure 11B:
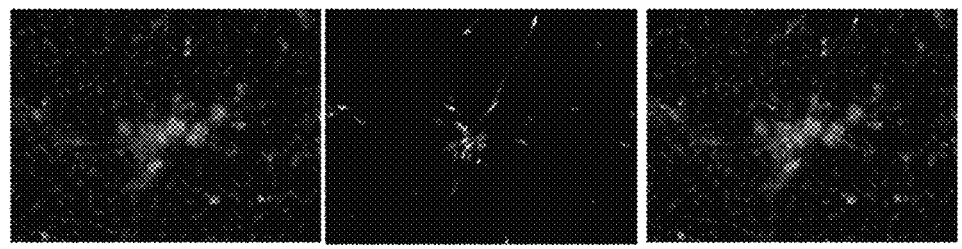
FIG. 11B shows an example of immunostaining images of a myelin marker (myelin basic protein (MBP)).
Figure 11B:
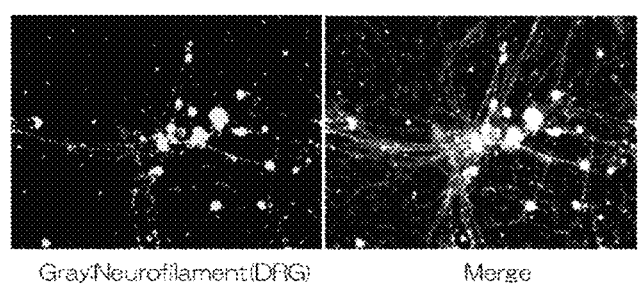
Figure 11B:
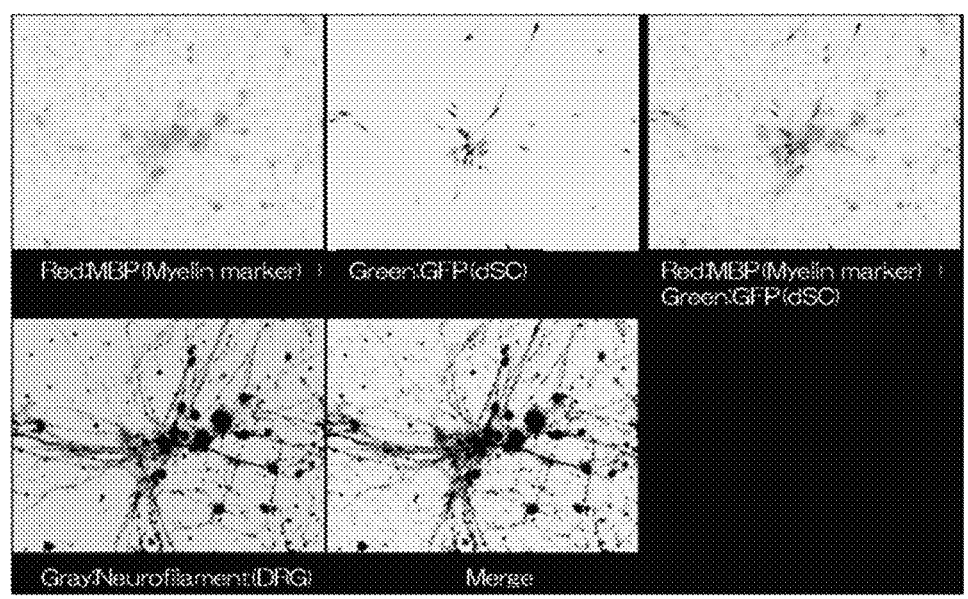

The cells after induction were positive for Schwann cell markers (S100β, GAP43) and an undifferentiated Schwann cell marker (p75NTR) (FIG. 10B).

Example 11 Myelination of dSC In Vitro by Co-Culture of GFP-Labeled dSC (dSC Induced by Introducing the Genes of Two Factors Sox10 and Krox20) with DRGn, Immuno-Fluorescent Staining Images of Cells for a Schwann-Cell-Related Marker (FIG. 11)

Myelinating ability of dSC in vitro by co-culture of GFP-labeled dSC with DRGn was evaluated.
Method
dSC cells were labeled with GFP using a retroviral vector.
Specifically, the cell marking was performed in accordance with the methods disclosed in the following documents: Yoshioka T, Ageyama N, Shibata H, Yasu T, Misawa Y, Takeuchi K, Matsui K, Yamamoto K, Terao K, Shimada K, Ikeda U, Ozawa K, Hanazono Y. Repair of infarcted myocardium mediated by transplanted bone marrow-derived CD34+stem cells in a nonhuman primate model. Stem Cells. 2005 March; 23(3): 355-64; and Hirschmann F and Verhoeyen E, Wirth D, Bauwens S, Hauser H, Rudert M. Vital marking of articular chondrocytes by retroviral infection using green fluorescence protein. Osteoarthritis Cartilage. 2002 February; 10(2): 109-18.

The dorsal root ganglion neuron (DRGn) cells obtained from postnatal day 5 mice were cultured in 12-well dishes and co-cultured with GFP-labeled dSC in a myelin differentiation-inducing medium containing nerve growth factors, ascorbic acid, and cAMP. Fourteen days after the start of co-culture of the genes, immunostaining was performed.

The medium used had the following composition: DMEM containing $N_2$ supplement (Invitrogen), 50 ng/ml ascorbic acid (Wako, Osaka, Japan), and 50 ng/ml recombinant rat b-nerve growth factor (NGF) (R&D Systems, Inc., Minneapolis, Minn., USA), and 0.5 μM cAMP (R&D Systems, Inc., Minneapolis, Minn., USA).

The medium was prepared in accordance with the following document: Sango K, Kawakami E, Yanagisawa H, Takaku S, Tsukamoto M, Utsunomiya K, Watabe K. Myelination in coculture of established neuronal and Schwann cell lines. Histochem Cell Biol. 2012 June; 137(6): 829-39.

The hosts of anti-neurofilament antibody (primary antibody) and anti-MBP (myelin basic protein) antibody (primary antibody) were mice. The hosts of anti-Tuj-1 antibody (primary antibody) and anti-protein zero antibody (primary antibody) were rabbits. As secondary antibodies, AlexaFluor566-conjugated anti-mouse IgG antibody, AlexaFluor566-conjugated anti-rabbit IgG antibody, Cy5-conjugated anti-mouse IgG antibody, and Cy5-conjugated anti-rabbit IgG antibody were used. The anti-MBP antibody and anti-protein zero antibody, which are myelin marker antibodies, were labeled in red. The anti-neurofilament antibody and anti-Tuj-1 antibody, which are nerve axon markers, were labeled in grey.

Result

FIG. 11 shows the results. Myelinated Schwann cells are observed along the nerve axon of DRG. Myelinated Schwann cells partially overlap with GFP-labeled dSC cells.

Example 12 Myelination In Vitro by Transplantation of GFP-Labeled dSC (dSC Induced by Introducing the Genes of Two Factors Sox10 and Krox20) into a Sciatic Nerve Crush Model, Immuno-Fluorescent Staining Images of Cells for a Myelin-Related Marker (FIG. 12)

The myelinating ability of dSC in vivo was examined.

Method dSC cells were labeled with GFP using a viral vector.

The sciatic nerve of each immunodeficient mouse was exposed and its center portion was grasped with Pean forceps for about 1 minute to crush the nerve in the range of about 5 mm. About 50,000 GFP-labeled dSCs were injected into the peripheral side. One month after the start of transplantation, the repaired nerve at the crushed site was collected and immunostained. FIG. 12 shows the outline of the method.

The host of anti-neurofilament antibody (primary antibody) and anti-MBP antibody (primary antibody) was a mouse. The host of anti-Tuj-1 antibody (primary antibody) and anti-protein zero antibody (primary antibody) was a rabbit. As secondary antibodies, AlexaFluor566-conjugated anti-mouse anti-rabbit IgG antibody and Cy5-conjugated anti-mouse anti-rabbit IgG antibody were used. The anti-MBP antibody and anti-protein zero antibody, which are myelin marker antibodies, were labeled in red. The anti-neurofilament antibody and anti-Tuj-1 antibody, which are nerve axon markers, were labeled in grey.

Results

FIG. 12 shows the results. The GFP+cells are observed along regenerating nerves and these overlap with the myelin marker+cells (FIGS. 12B and 12C).

Figure 12A:
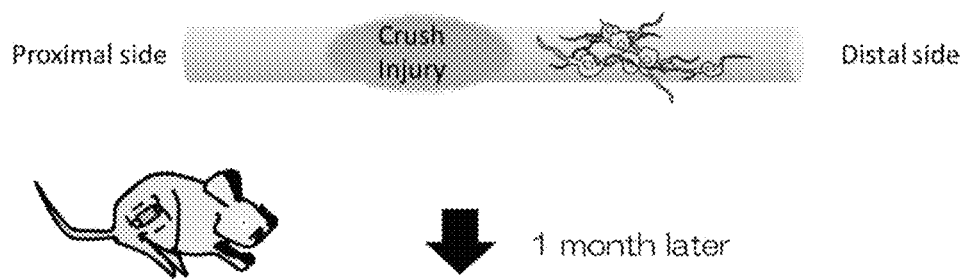
FIG. 12A outlines an evaluation test using a sciatic nerve crush model.
Figure 12A:
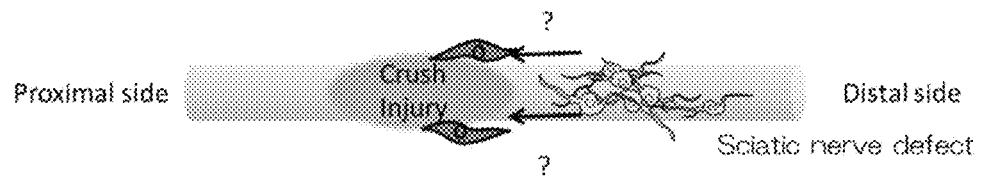
Figure 12B:
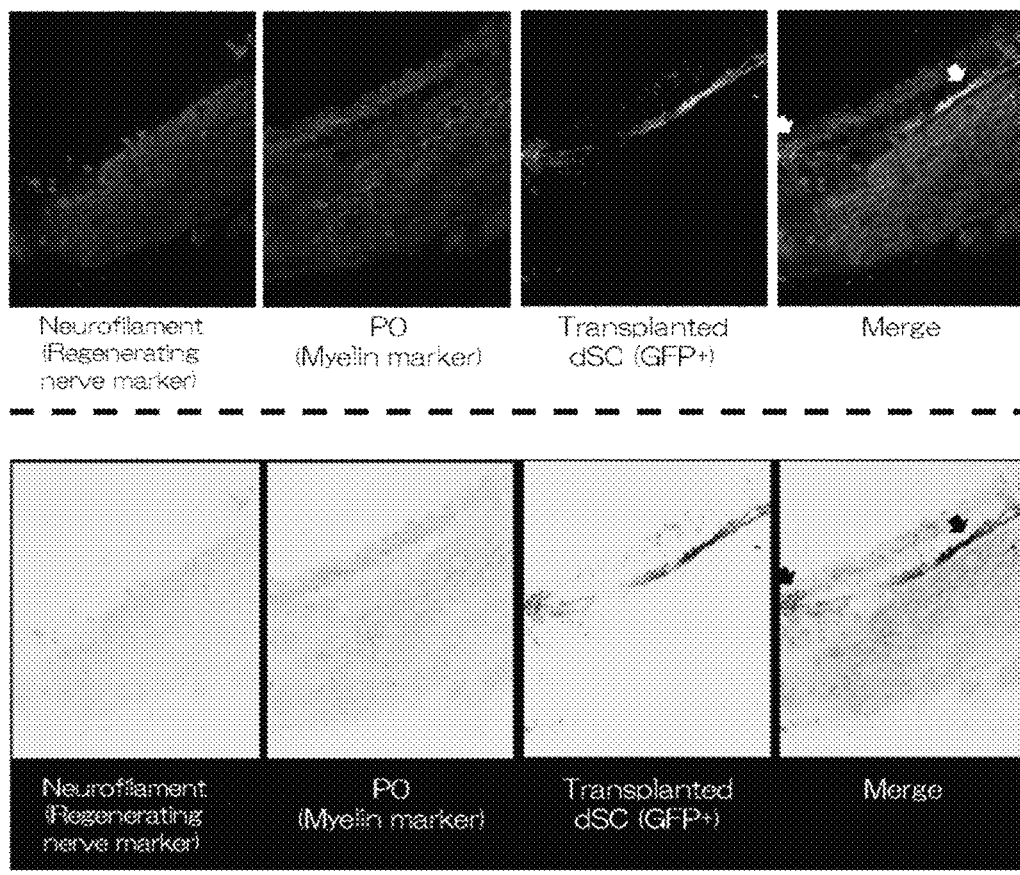
FIG. 12B shows an example of immunostaining images for Schwann cell-related markers.
Figure 12C:
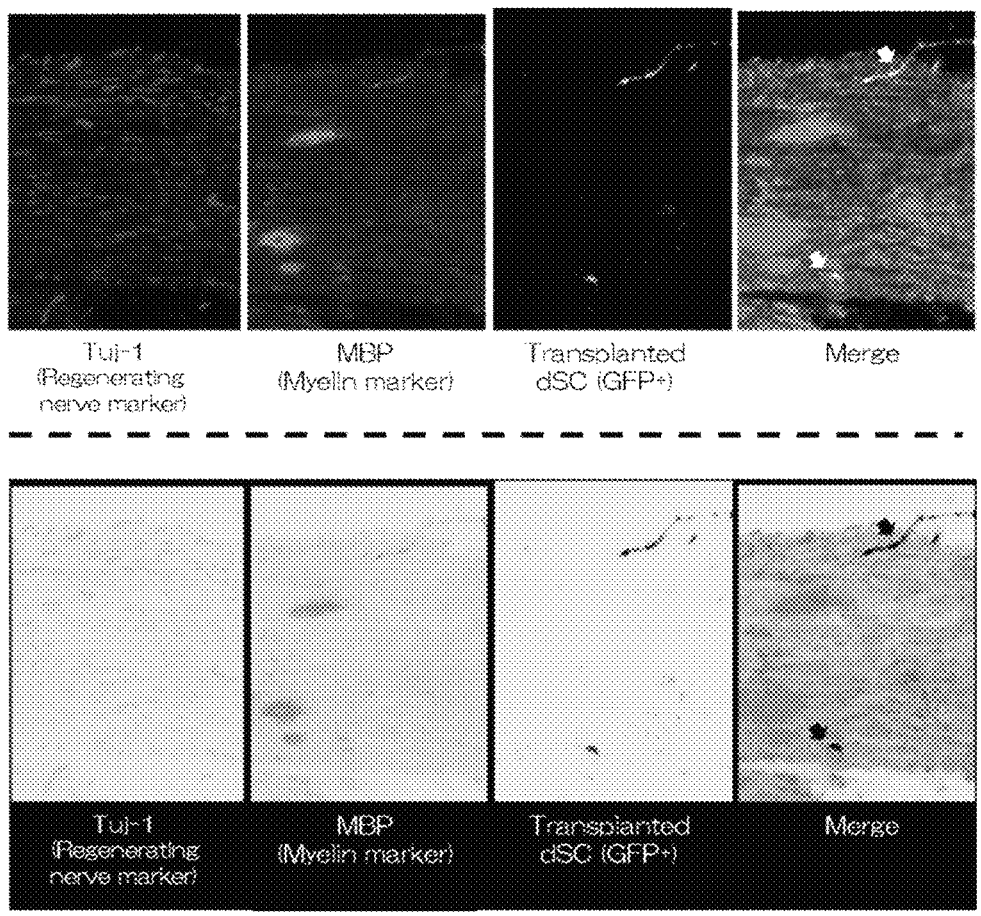
FIG. 12C shows an example of immunostaining images for Schwann cell-related markers.

The GFP+cells migrating into regenerating nerves expressed the myelin marker (FIGS. 12B and 12C, arrows).

Example 13 Transplantation of dSC into an Immunodeficient-Mouse Sciatic Nerve-Defect (5 mm) Model (FIG. 13)

Method

Cultured Schwann cells (SC: comparative control group) were separated from the sciatic nerve and cultured. These cells were seeded in a gelatin tube beforehand, and a gap of about 5 mm was formed in the sciatic nerve trunk of each mouse. The obtained hybrid tube was transplanted to the nerve defect site. Nerve regeneration promotion effects were evaluated in comparison with Sham-operated mice and with mice into which a tube containing only PBS was transplanted (FIG. 13A).

Figure 13A:
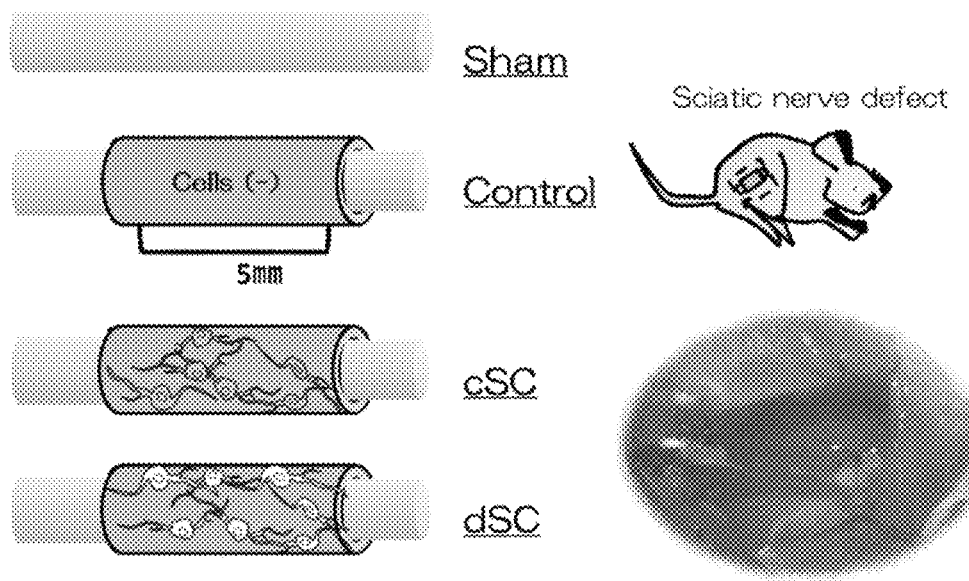
FIG. 13A outlines a transplantation test of dSC into an immunodeficient mouse sciatic nerve defect model.

FIG. 13A shows macroscopic images of bridged nerves and myelin stain images of the transverse section of regenerating nerve tissues using luxol fast blue. The sciatic nerve functions six weeks (6 w) and twelve weeks (12 w) after the transplantation are shown as the results. The atrophy of innervated muscle was evaluated based on wet muscle weight.

The sciatic functional index (SFI) was determined in accordance with the method disclosed in the following document: Inserra M M, Bloch D A, Terris D J. Functional indices for sciatic, peroneal, and posterior tibial nerve lesions in the mouse, Microsurgery, 1998; 18: 119-124.

The atrophy and fibrosis of innervated muscle were evaluated in accordance with the methods disclosed in the following document: Clavijo-Alvarez J A, Nguyen V T, Santiago L Y, Doctor J S, Lee W P, Marra K G. Comparison of biodegradable conduits within aged rat sciatic nerve defects. Plast Reconstr Surg. 2007; 119: 1839-1851.

Results

Figure 13B:
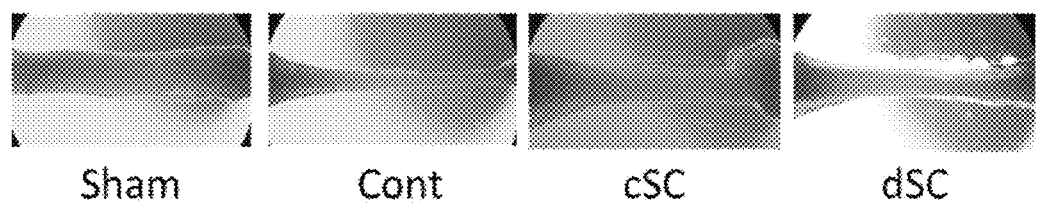
FIG. 13B shows macroscopic images of bridged nerves.

The macroscopic images of bridged nerves show that the cSC and dSC groups were both superior to the controls and that no clear difference was observed between the cSC and dSC groups (FIG. 13B).

Figure 13C:
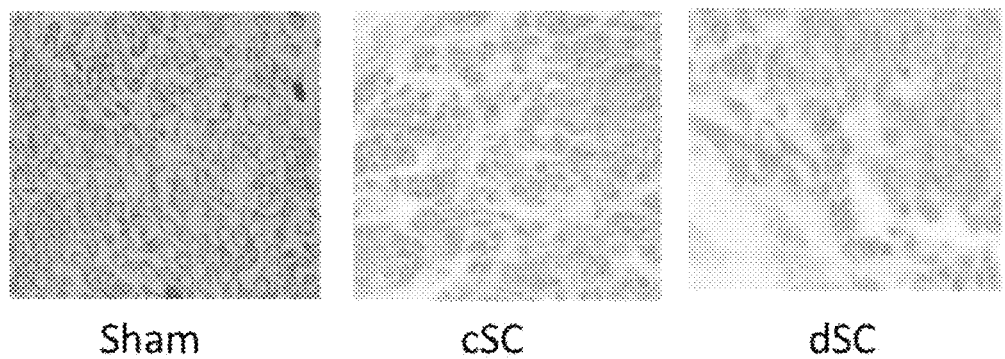
FIG. 13C shows myelin stain images of the transverse section of regenerating nerve tissue.

In the myelin stain images of the transverse section of regenerating nerve tissues using luxol fast blue, the dSC group was comparable to the cSC group (FIG. 13C).

Figure 13D:
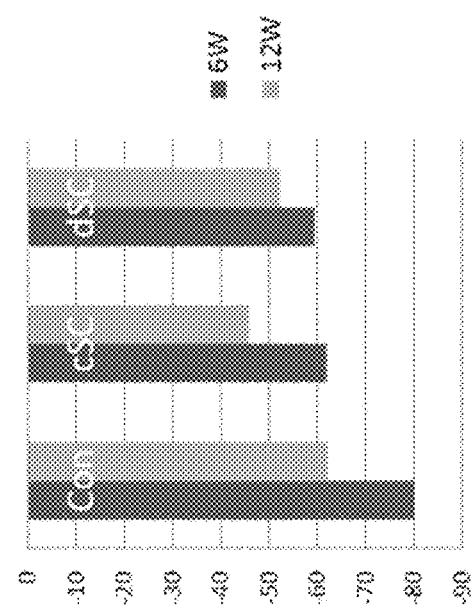
FIG. 13D shows evaluation results in terms of sciatic functional index (SFI).
Figure 13D:
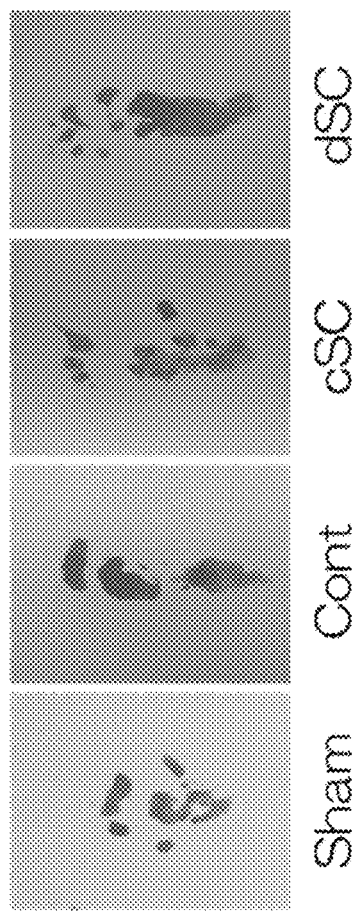

In the sciatic functional index (SFI), the recovery of sciatic nerve function in the dSC group at 12 weeks was comparable to that in the cSC group (FIG. 13D).

Figure 13E:
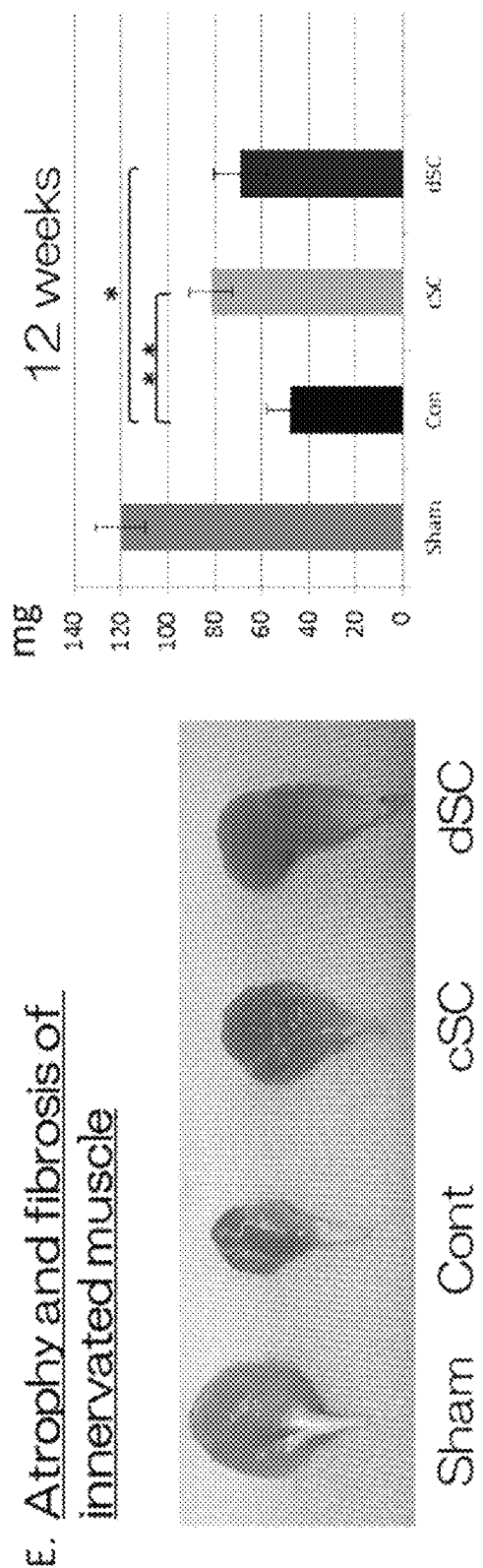
FIG. 13E shows evaluation results in terms of atrophy and fibrosis of innervated muscle.

Further, in terms of atrophy and fibrosis of the innervated muscle as well, the dSC and cSC groups were both significantly different from the control group, but no significant difference was observed between the cSC and dSC (FIG. 13E).

Example 14 Conversion into Schwann Cells (Table 2)

The same experiment as in Example 2 was performed using the combinations of genes shown in Table 2.

FIG. 2 shows which gene combination was introduced into which numbered well. (In the column of each gene in the table, "1" means that the cells were infected with a retroviral vector containing the gene, whereas a, blank means that the cells were not infected with a retroviral vector containing the gene.)

The plates were observed under a fluorescence microscope (produced by Olympus Corporation) in the same manner as in Example 3, and S100β staining was evaluated on a 4-point scale (+++, ++, +, − in descending order from the greatest number of S100β-positive cells).

Table 2 includes the evaluation results.

The results shows that although Oct6 is a factor known to perform important functions in the differentiation of Schwann cells, Oct6 is almost completely ineffective for inducing direct reprogramming from somatic cells into Schwann cells. The result further shows that Oct6 does not enhance the efficiency of direct reprogramming from somatic cells to Schwann cells achieved by using Sox10 alone, Krox20 alone, or a combination of Sox10 and Krox20.

TABLE 2

| | NO. | | | | | | | | | | | | | | | | | | |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 |
| Evaluation | + | + | − | +++ | + | − | ++ | + | + | − | + | − | − | − | − | − | + | − | − |
| Sox10 | 1 | | | 1 | 1 | | 1 | 1 | 1 | 1 | 1 | 1 | 1 | 1 | 1 | 1 | 1 | 1 | 1 |
| krox20 | | 1 | | 1 | | 1 | 1 | | | | | | | | | | | | |
| Oct6 | | | 1 | | 1 | 1 | 1 | | | | | | | | | | | | |
| Sox2 | | | | | | | | | 1 | | | | 1 | | 1 | 1 | | 1 | 1 |
| c-myc | | | | | | | | | | 1 | | | 1 | 1 | | | 1 | 1 | 1 |
| KLF4 | | | | | | | | | | | | 1 | | 1 | 1 | 1 | | 1 | |
| Oct4 | | | | | | | | | | | | | 1 | | 1 | | 1 | 1 | 1 |

| | NO. | | | | | | | | | | | | | | | | | | |
|---|---|---|---|---|---|---|---|---|---|---|---|---|---|---|---|---|---|---|---|
| | 38 | 39 | 40 | 41 | 42 | 43 | 44 | 45 | 46 | 47 | 48 | 49 | 50 | 51 | 52 | 53 | 54 | 55 | 56 |
| Evaluation | − | − | − | − | − | − | − | − | − | − | − | − | − | − | − | +++ | +++ | ++ | ++ |
| Sox10 | | | | | | | | | | | | | | | | 1 | 1 | 1 | 1 |
| krox20 | | | | | | | | | | | | | | | | 1 | 1 | 1 | 1 |
| Oct6 | 1 | | 1 | 1 | 1 | 1 | 1 | 1 | 1 | 1 | 1 | 1 | 1 | 1 | 1 | | | | |
| Sox2 | 1 | | | | 1 | | | 1 | 1 | | 1 | 1 | 1 | | 1 | 1 | | | |
| c-myc | | 1 | | | 1 | 1 | | | | 1 | 1 | 1 | | 1 | 1 | | 1 | | |
| KLF4 | | | 1 | | 1 | 1 | 1 | | | | 1 | 1 | 1 | 1 | 1 | | | 1 | |
| Oct4 | | | | 1 | | 1 | | 1 | 1 | | 1 | 1 | 1 | 1 | | | | | 1 |

| | NO. | | | | | | | | | | | | | | | | | |
|---|---|---|---|---|---|---|---|---|---|---|---|---|---|---|---|---|---|---|
| | 20 | 21 | 22 | 23 | 24 | 25 | 26 | 27 | 28 | 29 | 30 | 31 | 32 | 33 | 34 | 35 | 36 | 37 |
| Evaluation | − | − | − | − | − | − | − | − | − | − | − | − | − | − | − | − | − | − |
| Sox10 | 1 | 1 | 1 | | | | | | | | | | | | | | | |
| krox20 | | | | 1 | 1 | 1 | 1 | 1 | 1 | 1 | 1 | 1 | 1 | 1 | 1 | 1 | 1 | 1 |
| Oct6 | | | | | | | | | | | | | | | | | | |
| Sox2 | 1 | | 1 | 1 | | | 1 | | | | 1 | 1 | | 1 | 1 | 1 | | 1 |
| c-myc | | 1 | 1 | | 1 | | 1 | 1 | | | | 1 | 1 | | 1 | | 1 | 1 |
| KLF4 | 1 | 1 | 1 | | 1 | | | 1 | 1 | 1 | | | 1 | | 1 | 1 | 1 | 1 |
| Oct4 | 1 | 1 | 1 | | | 1 | | | | 1 | | 1 | | | 1 | 1 | 1 | 1 |

| | NO. | | | | | | | | | | | | | | | | | |
|---|---|---|---|---|---|---|---|---|---|---|---|---|---|---|---|---|---|---|
| | 57 | 58 | 59 | 60 | 61 | 62 | 63 | 64 | 65 | 66 | 67 | 68 | 69 | 70 | 71 | 72 | 73 | 74 |
| Evaluation | ++ | ++ | ++ | ++ | + | ++ | ++ | ++ | +++ | ++ | ++ | + | + | + | + | + | + | + |
| Sox10 | 1 | 1 | 1 | 1 | 1 | 1 | 1 | 1 | 1 | 1 | 1 | 1 | 1 | 1 | 1 | 1 | 1 | 1 |
| krox20 | 1 | 1 | 1 | 1 | 1 | 1 | 1 | 1 | 1 | 1 | 1 | | | | | | | |
| Oct6 | | | | | | | | | | | | 1 | 1 | 1 | 1 | 1 | 1 | 1 |
| Sox2 | 1 | | | 1 | 1 | | 1 | 1 | 1 | | 1 | 1 | | | | 1 | | |
| c-myc | 1 | 1 | | | | 1 | 1 | 1 | | 1 | 1 | | 1 | | | 1 | 1 | |
| KLF4 | | 1 | 1 | 1 | | | 1 | | 1 | 1 | 1 | | | 1 | | | 1 | 1 |
| Oct4 | | | 1 | | 1 | 1 | | 1 | 1 | 1 | 1 | | | | 1 | | | 1 |

| | NO. | | | | | | | | | | | | | | | | | | |
|---|---|---|---|---|---|---|---|---|---|---|---|---|---|---|---|---|---|---|---|
| | 75 | 76 | 77 | 78 | 79 | 80 | 81 | 82 | 83 | 84 | 85 | 86 | 87 | 88 | 89 | 90 | 91 | 92 | 93 | 94 |
| Evaluation | + | + | + | + | + | + | + | + | − | − | − | − | − | − | − | − | − | − | − | − |
| Sox10 | 1 | 1 | 1 | 1 | 1 | 1 | 1 | 1 | | | | | | | | | | | | |
| krox20 | | | | | | | | | 1 | 1 | 1 | 1 | 1 | 1 | 1 | 1 | 1 | 1 | 1 | 1 |
| Oct6 | 1 | 1 | 1 | 1 | 1 | 1 | 1 | 1 | 1 | 1 | 1 | 1 | 1 | 1 | 1 | 1 | 1 | 1 | 1 | 1 |
| Sox2 | 1 | 1 | | 1 | 1 | 1 | | 1 | 1 | | | | 1 | | | 1 | 1 | | 1 | 1 |
| c-myc | | | 1 | 1 | | 1 | 1 | 1 | | 1 | | | 1 | | | | | 1 | 1 | 1 |
| KLF4 | 1 | | | 1 | | 1 | 1 | 1 | | | 1 | | 1 | 1 | 1 | | | 1 | | |
| Oct4 | | 1 | 1 | | 1 | 1 | 1 | 1 | | | | 1 | | | 1 | | 1 | 1 | | 1 |

| | NO. | | | | | | | | | | | | | | | | | |
|---|---|---|---|---|---|---|---|---|---|---|---|---|---|---|---|---|---|---|
| | 95 | 96 | 97 | 98 | 99 | 100 | 101 | 102 | 103 | 104 | 105 | 106 | 107 | 108 | 109 | 110 | 111 | 112 |
| Evaluation | − | − | − | ++ | ++ | + | ++ | + | + | + | ++ | ++ | + | ++ | + | + | + | − |
| Sox10 | | | | 1 | 1 | 1 | 1 | 1 | 1 | 1 | 1 | 1 | 1 | 1 | 1 | 1 | 1 | 1 |
| krox20 | 1 | 1 | 1 | 1 | 1 | 1 | 1 | 1 | 1 | 1 | 1 | 1 | 1 | 1 | 1 | 1 | 1 | 1 |
| Oct6 | 1 | 1 | 1 | 1 | 1 | 1 | 1 | 1 | 1 | 1 | 1 | 1 | 1 | 1 | 1 | 1 | 1 | 1 |
| Sox2 | 1 | | 1 | 1 | | | 1 | | | 1 | 1 | | 1 | 1 | | | 1 | |
| c-myc | | 1 | 1 | | 1 | | 1 | 1 | | | | 1 | 1 | | | | 1 | 1 |
| KLF4 | 1 | 1 | | | 1 | | | 1 | 1 | | | 1 | | | 1 | | 1 | 1 |
| Oct4 | 1 | 1 | 1 | | | 1 | | | 1 | | 1 | | | 1 | | 1 | | 1 |

Example 15 Production of Neurotrophic Factor
(FIG. 14)

The HDF, cSC, and dSC were seeded in cell culture dishes at a concentration of $4\times10^4$ cells/cm$^2$. After continuing 80% confluence, the cells were cultured in media for harvesting cell supernatants for 48 hours. After the culture supernatant of each group was passed through a 40-μm filter, the filtrate was collected. The amounts of the following proteins in the culture supernatants of the cultured cells were measured using ELISA kits for human BDNF, GDNF, and NGF (Promega, Madison, Wis.): brain-derived neurotrophic factor (BDNF), glial-cell-line-derived neurotrophic factor (GDNF), and nerve growth factor (NGF).

The results show that the cSC and dSC strongly produced BDNF, GDNF, and NGF, compared to the control (HDF). Further, cSC and dSC are similar in that the production of BDNF is the highest.

The invention claimed is:

1. A method for generating a Schwann cell comprising introducing into a somatic cell of a mammal a combination of SOX10 gene or an expression product thereof and KROX20 gene or an expression product thereof, wherein the somatic cell is a fibroblast or a vascular endothelial cell, and wherein the Schwann cell is directly induced from the somatic cell without first becoming a multipotent stem cell.

2. A grafting material for treating a disease based on a nerve defect, or a defect, deficiency, or hypofunction of Schwann cells, the grafting material comprising a cell obtained by the method according to claim 1.

* * * * *